United States Patent
Chen

(10) Patent No.: US 10,792,341 B2
(45) Date of Patent: *Oct. 6, 2020

(54) TREATMENT OF GLYCOGEN STORAGE DISEASE TYPE II

(71) Applicant: Duke University, Durham, NC (US)

(72) Inventor: Yuan-Tsong Chen, Chapel Hill, NC (US)

(73) Assignee: Duke University, Durham, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/876,086

(22) Filed: Jan. 19, 2018

(65) Prior Publication Data
US 2018/0185457 A1 Jul. 5, 2018

Related U.S. Application Data

(63) Continuation of application No. 15/066,211, filed on Mar. 10, 2016, now Pat. No. 9,907,839, which is a continuation of application No. 14/485,071, filed on Sep. 12, 2014, now Pat. No. 9,370,556, which is a continuation of application No. 13/593,148, filed on Aug. 23, 2012, now Pat. No. 8,900,552, which is a continuation of application No. 13/064,556, filed on Mar. 30, 2011, now abandoned, which is a continuation of application No. 12/604,267, filed on Oct. 22, 2009, now abandoned, which is a continuation of application No. 11/889,457, filed on Aug. 13, 2007, now abandoned, which is a continuation of application No. 11/039,281, filed on Jan. 20, 2005, now abandoned, which is a continuation of application No. 09/902,461, filed on Jul. 10, 2001, now Pat. No. 7,056,712.

(60) Provisional application No. 60/219,237, filed on Jul. 18, 2000.

(51) Int. Cl.
*A61K 38/47* (2006.01)
*A61K 45/06* (2006.01)
*A61K 38/00* (2006.01)

(52) U.S. Cl.
CPC .............. *A61K 38/47* (2013.01); *A61K 45/06* (2013.01); *C12Y 302/0102* (2013.01); *A61K 38/00* (2013.01)

(58) Field of Classification Search
CPC ... A61K 38/47; A61K 45/06; C12Y 302/0102
See application file for complete search history.

(56) References Cited

U.S. PATENT DOCUMENTS

| | | | |
|---|---|---|---|
| 5,356,804 A | 10/1994 | Desnick et al. | |
| 5,880,091 A | 3/1999 | Cummings | |
| 6,118,045 A | 9/2000 | Reuser et al. | |
| 6,537,785 B1 | 3/2003 | Canfield | |
| 7,056,712 B2 * | 6/2006 | Chen | A61K 38/47 435/183 |
| 7,351,410 B2 | 4/2008 | Van Bree et al. | |
| 7,629,309 B2 | 12/2009 | LeBowitz et al. | |
| 7,655,226 B2 | 2/2010 | Van Bree | |
| 8,470,552 B2 | 6/2013 | Croughan et al. | |
| 8,900,552 B2 * | 12/2014 | Chen | A61K 38/47 424/9.1 |
| 9,370,556 B2 * | 6/2016 | Chen | A61K 38/47 |
| 9,907,839 B2 * | 3/2018 | Chen | A61K 38/47 |
| 2004/0081645 A1 | 4/2004 | Van Bree et al. | |
| 2005/0244400 A1 | 11/2005 | LeBowitz et al. | |
| 2013/0195834 A1 | 8/2013 | Chen et al. | |

FOREIGN PATENT DOCUMENTS

| | | |
|---|---|---|
| EP | 1224266 | 9/2007 |
| WO | WO1997/05771 | 2/1997 |
| WO | WO1999/58691 | 11/1999 |
| WO | WO2000/34451 | 6/2000 |

OTHER PUBLICATIONS

Myozyme Formulary Information. Exhibit 2077 in *BioMarin* v. *Duke University* IPR2013-00535, filed by Duke on May 22, 2014.
Prosecution history of U.S. Pat. No. 7,351,41 0. Exhibit 2079 in *BioMarin* v. *Duke University* IPR2013-00535, filed by Duke on May 22, 2014.
"FDA Approves First Treatment for Pompe Disease," Apr. 28, 2006, at www.fda.gov/NewsEvents/Newsroom/PressAnnouncements/2006/ucm1 08645.htm, as accessed on May 15, 2014. Exhibit 2032 in *BioMarin* v. *Duke University* IPR2013-00535, filed by Duke on May 22, 2014.
"FDA Approves New Treatment for Late-Onset Pompe Disease," May 25, 2010, at http://www.fda.gov/NewsEvents/Newsroom/PressAnnouncements/ucm213282.htm, as accessed on May 15, 2014. Exhibit 2034 in *BioMarin* v. *Duke University* IPR2013-00535, filed by Duke on May 22, 2014.
Petition for Inter Partes Review of U.S. Pat. No. 7,056,712 (filed Aug. 28, 2013). Paper 5 in *BioMarin* v. *Duke University* IPR2013-00535, filed by BioMarin on Aug. 28, 2013.
Duke Preliminary Response (filed Dec. 4, 2013). Paper 13 in *BioMarin* v. *Duke University* IPR2013-00535, filed by Duke on Dec. 4, 2013.
PTAB's Decision Instituting Inter Partes Review. Paper 16 in *BioMarin* v. *Duke University* IPR2013-00535, entered by the PTAB on Feb. 24, 2014.
Duke's Patent Owner Response. Paper 59 in *BioMarin* v. *Duke University* IPR2013-00535, filed by Duke on May 22, 2014.
Declaration of Dwight Koeberl, M.D., Ph.D., dated Oct. 9, 2012, filed as Document D45 in the EPO Opposition Proceeding of Patent No. EP1301201 (Application No. 01951 000.7). Exhibit 1138 in *BioMarin* v. *Duke University* IPR2013-00535, served by BioMarin on Apr. 21, 2014.
Declaration of Gregory M. Pastores, MD. dated Aug. 26, 2013. Exhibit 1020 in *BioMarin* v. *Duke University* IPR2013-00535, filed by BioMarin on Sep. 10, 2013.

(Continued)

*Primary Examiner* — Karen Cochrane Carlson
(74) *Attorney, Agent, or Firm* — McDonnell Boehnen Hulbert & Berghoff LLP

(57) ABSTRACT

Methods of treating glycogen storage disease type II, by administering acid α-glucosidase, are described, as are compositions for use in treatment of glycogen storage disease type II.

2 Claims, 5 Drawing Sheets

(56) References Cited

OTHER PUBLICATIONS

Declaration of Matthew Croughan, Ph.D. dated Aug. 27, 2013. Exhibit 1021 in *BioMarin v. Duke University* IPR2013-00535, filed by BioMarin on Sep. 10, 2013.
Supplemental Declaration of Gregory M. Pastores, M.D. dated Mar. 28, 2014. Exhibit 1133 in *BioMarin v. Duke University* IPR2013-00535, served by BioMarin on Mar. 31, 2014.
Supplemental Declaration of Matthew Croughan, Ph.D. dated Mar. 25, 2014. Exhibit 1134 in *BioMarin v. Duke University* IPR2013-00535, served by BioMarin on Mar. 31, 2014.
Transcript of the Deposition of MatthewS. Croughan, Ph.D. dated Apr. 22, 2014. Exhibit 1141 in *BioMarin v. Duke University* IPR2013-00535, filed by BioMarin on May 30, 2014.
Transcript of the Deposition of Gregory M. Pastores, M.D. dated Apr. 29, 2014. Exhibit 1142 in *BioMarin v. Duke University* IPR2013-00535, filed by BioMarin on May 30, 2014.
Declaration of Matthew Croughan, Ph.D. in *BioMarin v. Genzyme* IPR2013-00534 (as Exhibit 1 033), dated Aug. 27, 2013. Exhibit 2014 in *BioMarin v. Duke University* IPR2013-00535, filed by Duke on May 22, 2014.
Transcript of the Deposition of Gregory M. Pastores, M.D. in IPR2013-00534 (as Exhibit 1162), dated May 9, 2014. pp. 1-150. Exhibit 2033 in *BioMarin v. Duke University* IPR2013-00535, filed by Duke on May 22, 2014.
Transcript of the Deposition of Gregory M. Pastores, M.D. in IPR2013-00534 (as Exhibit 1162), dated May 9, 2014. pp. 151-266. Exhibit 2033 in *BioMarin v. Duke University* IPR2013-00535, filed by Duke on May 22, 2014.
Transcript of the Deposition of MatthewS. Croughan, Ph.D. dated Apr. 16, 2014 in *BioMarin v. Genzyme* IPR2013-00534 (as Exhibit 1161 ). Exhibit 2013 in *BioMarin v. Duke University* IPR2013-00535, filed by Duke on May 22, 2014.
Declaration of Barry J. Byrne, M.D., Ph.D., dated Nov. 16, 2012, filed by Opponent Zystor via letter dated Nov. 21, 2012 in the EPO Opposition Proceeding of Patent No. EP1301201 (Application No. 01951000.7).
Cover letter for the filing of the Declaration of Barry J. Byrne, M.D., Ph.D., dated Nov. 16, 2012, filed by Opponent Zystor via letter dated Nov. 21, 2012 in the EPO Opposition Proceeding of Patent No. EP1301201 Application No. 01951 000.7).
Declaration of Richard D. Cummings, Ph.D., dated Nov. 29, 2010, filed by Patentee Duke as Document D8 in the EPO Opposition Proceeding of Patent No. EP1301201 Application No. 01951000.7).
Declaration of Arthur L. Caplan, Ph.D., dated Oct. 9, 2012, filed by Patentee as Document D44 in the EPO Opposition Proceeding of Patent No. EP1301201 (Application No. 01951000.7).
Second Declaration of Richard D. Cummings, Ph.D., dated Jun. 9, 2013, filed by Patentee Duke as Document D99 in the EPO Opposition Proceeding of Patent No. EP1301201 (Application No. 01951 000.7).
Declaration of Yuan-Tsong Chen, M.D., Ph.D., dated Jun. 6, 2013, filed by Patentee Duke as Document D98 in the EPO Opposition Proceeding of Patent No. EP1301201 Application No. 01951000.7).
Declaration of Dwight Koeberl, M.D., Ph.D., dated Jun. 9, 2013, filed by Patentee Duke as Document D1 00 in the EPO Opposition Proceeding of Patent No. EP1301201 Application No. 01951000.7).
Declaration of Melissa Wasserstein, M.D., dated May 22, 2014, filed by Patentee Duke as Exhibit 2019 in *BioMarin v. Duke University* IPR2013-00535 on May 22, 2014.
Declaration of Richard D. Cummings, Ph.D., dated May 22, 2014, filed by Patentee Duke as Exhibit 2020 in *BioMarin v. Duke University* IPR2013-00535 on May 22, 2014.
Declaration of Philip Green, dated May 22, 2014, filed by Patentee Duke as Exhibit 2021 in *BioMarin v. Duke University* IPR2013-00535 on May 22, 2014.
Letter of Oct. 17, 2012 from the Patentee Duke to the EPO in the EPO Opposition Proceeding of Patent No. EP1301201 (Application No. 01951 0001).
Claims from Duke's Japanese Patent Application No. 2002-511773.
Oct. 4, 2012 Decision of the Appeal Board of the Japanese Patent Office (English Translation) in Duke's Japanese Patent Application No. 2002-511773.
Declaration of Richard D. Cummings, Ph.D., dated Aug. 20, 2011, and filed by Duke in the Japanese Patent Application No. 2002-511773.
Second Declaration of Richard D. Cummings, Ph.D. dated Jun. 10, 2012, and filed by Duke in the Japanese Patent Application No. 2002-511773.
Third Party Provision of Information, dated Aug. 8, 2012, submitted by Zystor in the Japanese Patent Application No. 2002-511773.
Assignment of Assignor's Interest executed by Yuan-Tsong Chen on Oct. 18, 2000, as filed in the EPO Opposition Proceeding of Patent No. EP1301201 (Application No. 01951 000.7).
Amoresano et al., "The carbohydrates of the isoforms of three avian riboflavin-binding proteins," Eur. J. Biochem. 263:849-858 (1999).
Anson et al., "Correction of human mucopolysaccharidosis type-VI fibroblasts with recombinant N-acetylgalactosamine-4-sulphatase," Biochem. J., 284:789-94 (1992). Exhibit 1109 in *BioMarin v. Duke University* IPR2013-00535, filed by BioMarin on Sep. 10, 2013.
Ashwell & Harford, "Carbohydrate-specific receptors of the liver," Annu. Rev. Biochem. 51 :531-554 (1982).
Banga, A. K., Pharmaceutical Biotechnology: The Arrival of Recombinant Proteins, Lancaster, Technomic Publishing Co., Inc., 1995, 3-28. Exhibit 1066 in *BioMarin v. Duke University* IPR2013-00535, filed by BioMarin on Sep. 10, 2013.
Banga, A. K., Formulation of Therapeutic Peptides and Proteins—Formulation, Process and Delivery Systems, Ed. A. K. Banga, Lancaster, Technomic Publishing Co., Inc., 1995, 81-129. Exhibit 1093 in *BioMarin v. Duke University* IPR2013-00535, filed by BioMarin on Sep. 10, 2013.
Barton et al., "Replacement Therapy for Inherited Enzyme Deficiency—Macrophagetargeted Glucocerebrosidase for Gaucher's Disease," N. Eng. J. Med., 324:1464-1470 (May 23, 1991). Exhibit 1009 in *BioMarin v. Duke University* IPR2013-00535, filed by BioMarin on Sep. 10, 2013.
Baudhuin et al., "An electron microscopic and biochemical study of type II glycogenosis," Lab. Invest., 13:1139-52 (1964). Exhibit 1049 in *BioMarin v. Duke University* IPR2013-00535, filed by BioMarin on Sep. 10, 2013.
Bembi et al., "Enzyme replacement therapy in type 1 and type 3 Gaucher's disease," The Lancet, 344:1679-1682 (Dec. 17, 1994). Exhibit 1008 in *BioMarin v. Duke University* IPR2013-00535, filed by BioMarin on Sep. 10, 2013.
Bennett, W. F., "Two forms of tissue-type plasminogen activator (tpa) differ at a single specific glycosylation site," Thrombosis and Haemostasis, vol. 50, No. 0315, 1983. Exhibit 1085 in *BioMarin v. Duke University* IPR2013-00535, filed by BioMarin on Sep. 10, 2013.
Berggard & Beam, "The Hurler Syndrome—A Biochemical and Clinical Study" Am. J. Med., 39:221-29 (1965). Exhibit 2029 in *BioMarin v. Duke University* IPR2013-00535, filed by Duke on May 22, 2014.
Bibila, T. A. and D. K. Robinson, "In Pursuit of the Optimal Fed-Batch Process for Monoclonal Antibody Production," Biotechnol. Prog., 11 (1):1-13 (1995). Exhibit 1078 in *BioMarin v. Duke University* IPR2013-00535, filed by BioMarin on Sep. 10, 2013.
Bielicki et al., "Recombinant human iduronate2-sulphatase: correction of mucopolysaccharidosis-type II fibroblasts and characterization of the purified enzyme," Biochem. J., 289: 241-46 (1993). Exhibit 1110 in *BioMarin v. Duke University* IPR2013-00535, filed by BioMarin on Sep. 10, 2013.
Bivjoet et al., "Expression of eDNA-encoded human acid alpha-glucosidase in milk of transgenic mice," Biochimica et Biophysica Acta, 1308:93-96 (Aug. 1996). Exhibit 1036 in *BioMarin v. Duke University* IPR2013-00535, filed by BioMarin on Sep. 10, 2013.
Bivjoet et al., "Generalized glycogen storage and cardiomegaly in a knockout mouse model of Pompe disease," Human Molecular Genetics, 7:53-62 (Jan. 1998). Exhibit 1037 in *BioMarin v. Duke University* IPR2013-00535, filed by BioMarin on Sep. 10, 2013.
"China Synthetic Rubber to Collect Huge Royalty From Orphan Drug", China Economic News Service, Oct. 4, 2006, at http://www.m2mevolution.com/news/2006/10/04/1960188.htm, as accessed on

(56) References Cited

OTHER PUBLICATIONS

May 20, 2014. Exhibit 2061 in *BioMarin v. Duke University* IPR2013-00535, filed by Duke on May 22, 2014.
U.S. Court of Appeals for the Federal Circuit, *Duke University v. Biomarin Pharmaceutical Inc.*, decided Apr. 25, 2017, pp. 1-22 (*Duke Univ. v. BioMarin Pharm.*, 685 Fed. Appx. 967 (Fed. Cir. Apr. 25, 2017)).
U.S. Court of Appeals for the Federal Circuit, Brief of Appelle in *Duke University v. Biomarin Pharmaceutical Inc.*, IPR2013-00535, filed by BioMarin Pharm on May 27, 2016, pp. 1-75.
U.S. Court of Appeals for the Federal Circuit, Reply Brief for Appellant in *Duke University v. Biomarin Pharmaceutical Inc.*, IPR2013-0535, filed by Duke University on Aug. 9, 2016, pp. 1-42.
U.S. Court of Appeals for the Federal Circuit, Brief for Appellant in *Duke University v. Biomarin Pharmaceutical Inc.*, IPR2013-0535, filed by Duke University on Feb. 19, 2016, pp. 1-163.
Van der Ploeg et al., "Glycogenosis type II: protein and DNA analysis in five South African families from various ethnic origins", Am. J. Hum. Genet. 44(6):787-793 (Jun. 1989).
Wenger & Williams, "Screening for lysosomal disorders" in Hommes, F. A. (ed.), Techniques in diagnostic human biochemical genetics: a laboratory manual, Wiley-Liss, New York, 1991, pp. 587-617.
Hug & Schubert, Hepatic lysozymes in Pompe's disease: Disappearance during glucosidase administration. J. Clin. Invest 46(6):1073 (Jun. 1967).
Pharming Press Release, (Mar. 15, 2000) Pharming's first Phase-II clinical trian for Pompe's disease finalised showing survival, skeletal muscle regeneration and overall improvement of heart and lung functions. pp. 1-3.
Press Release (Feb. 14, 1998) Duke Researchers Develop First Treatment for Rare Muscle Disease. pp. 1-3.
U.S. Appl. No. 60/153,831, filed Sep. 14, 1999 to Canfield et al.
Messinger et al., "Successful immune tolerance induction to enzyme replacement therapy in CRIM-negative infantile Pompe disease," Genetics in Medicine 14(1):135-142 (2012).
Bollack, "Biotechnology venture hits unexpected snags," The New York Times, Nov. 23, 2001.
Benzyme General 2002 Annual Report, selected pages.
EPO office action dated Feb. 26, 2014, entered in the prosecution of EPO patent application No. EP 07001091.3.
Applicant's Response to Office Action, dated Mar. 18, 2014, filed by Duke in the prosecution of EPO patent application No. EP 07001091.3.
EPO's Intent to Grant a European Patent in the EPO patent application No. EP 07001091.3, entered on Jun. 2, 2014.
Hug & Schubert, "Hepatic Lysosomes in Pompe's Disease: Disappearance during Glucosidase Administration," J. Clin. IInvest., 46:1073 (1967). Exhibit 2035 in *BioMarin v. Duke University* IPR2013-00535, filed by Duke on May 22, 2014. Part 1 of 2.
Hug & Schubert, "Hepatic Lysosomes in Pompe's Disease: Disappearance during Glucosidase Administration," J. Clin. Invest., 46:1073 (1967). Exhibit 2035 in *BioMarin v. Duke University* IPR2013-00535, filed by Duke on May 22, 2014. Part 2 of 2.
Opponent's reply filed by Zystor on Oct. 14 and 16, 2013 in the EPO Opposition Proceeding of Patent No. EP1301201 (Application No. 01951 0001).
Opponent's observation filed by Zystor on Oct. 30, 2012 in the EPO Opposition Proceeding of Patent No. EP1301201 (Application No. 01951 0001).
Patentee's response filed by Duke on Nov. 20, 2012 in the EPO Opposition Proceeding of Patent No. EP1301201 (Application No. 01951 0001).
Transcript of the Deposition of Richard D. Cummings, Ph.D., dated Jul. 1, 2014, in *BioMarin v. Duke University* IPR2013-00535.
Transcript of the Deposition of Melissa Wasserstein, M.D., dated Jul. 17, 2014, in *BioMarin v. Duke University* IPR2013-00535.
Crawley et al., "Enzyme Replacement Therapy in a Feline Model of Maroteaux-Lamy Syndrome," J. Clin. Invest. 97:1864-1873 (1996).

Exhibit 1154 in *BioMarin v. Duke University* IPR2013-00535, as provided by BioMarin on Jul. 17, 2014.
Kakkis et al., "Long-Term and High-Dose Trials of Enzyme Replacement Therapy in the Canine Model of Mucopolysaccharidosis 1," Biochem. Mol. Med. 58:156-167 (1996). Exhibit 1155 in *BioMarin v. Duke University* IPR2013-00535, as provided by BioMarin on Jul. 17, 2014.
BioMarin's Petitioner Reply to Duke's Patent Owner Response. Paper 67 in *BioMarin v. Duke University* IPR2013-00535, filed by BioMarin on Aug. 14, 2014.
Transcript of the Deposition of William Canfield, M.D., dated Jun. 26, 2014. Exhibit 1157 in *BioMarin v. Duke University* IPR2013-00535, filed by BioMarin on Aug. 14, 2014.
Amendment in U.S. Appl. No. 10/611,598. Exhibit 1158 in *BioMarin v. Duke University* IPR2013-00535, filed by BioMarin on Aug. 14, 2014.
U.S. Appl. No. 10/611,598. Exhibit 1159 in *BioMarin v. Duke University* IPR2013-00535, filed by BioMarin on Aug. 14, 2014.
Patent Term Extension Approval Letter for Myozyme for U.S. Pat. No. 6,118,045 of Reuser (Oct. 16, 2008). Exhibit 1160 in *BioMarin v. Duke University* IPR2013-00535, filed by BioMarin on Aug. 14, 2014.
Physicians' Desk Reference, 52 Ed., Listings for Ceredase® and Cerezyme® 1998. Exhibit 1161 in *BioMarin v. Duke University* IPR2013-00535, filed by BioMarin on Aug. 14, 2014.
Enbrel Package Insert (Nov. 1998). Exhibit 1162 in *BioMarin v. Duke University* IPR2013-00535, filed by BioMarin on Aug. 14, 2014.
Herceptin 1998 Label. Exhibit 1163 in *BioMarin v. Duke University* IPR2013-00535, filed by BioMarin on Aug. 14, 2014.
1992 Orphan Drug Regulations, Fed. Reg., vol. 57, No. 250, 62076-62092 (Dec. 29, 1992). Exhibit 1164 in *BioMarin v. Duke University* IPR2013-00535, filed by BioMarin on Aug. 14, 2014.
Brooks, Immune Response to Enzyme Replacement Therapy in Lysosomal Storage Disorder Patients and Animal Models, Molecular Genetics and Metabolism, 68, 268-275 (1999). Exhibit 1165 in *BioMarin v. Duke University* IPR2013-00535, filed by BioMarin on Aug. 14, 2014.
*EMC Corporation v. PersonaiWeb Technologies, LLC* (PTAB Case IPR2013-00083, Paper No. 80 (PTAB May 15, 2014). Exhibit 1166 in *BioMarin v. Duke University* IPR2013-00535, filed by BioMarin on Aug. 14, 2014.
Van den Hout et al, "Recombinant human alpha-glucosidase from rabbit milk in Pompe patients", The Lancet 356:397-398 (2000).
Ding et al, "Long-Term Efficacy after [El-, polymerase-] Adenovirus-Mediated Transfer of Human Acid-alpha-Glucosidase Gene into Glycogen Storage Disease Type II Knockout Mice", Human Gene Therapy 12:955-965 (2001).
Synpac Press Release (Jun. 30, 1999) Duke University starts clinical trials for Pompe's disease (cited in Opposition filed in connection with corresponding European Patent No. EP1301201).
Press Release (Apr. 19, 2000) Genzyme General Obtains Rights to Pompe Disease Therapy from Synpac (cited in Opposition filed in connection with corresponding European Patent No. EP1301201).
Nilsson et al, "Induction of immune tolerance in patients with hemophilia and antibodies to factor VIII by combined treatment with intravenous IgG, cyclophosphamide, and factor VIII", The New England J of Medicine, 1988, 318:947-950.
Poenaru, L., Approach to Gene Therapy of Glycogenosis Type II (Pompe Disease), Molecular Genetics and Metabolism, 70(3): 163-169 (2000).
Hirschhorn, R., "Glycogen Storage Disease Type II: Acid alpha-Glucosidase (Acid Maltase) Deficiency", The Metabolic and Molecular Bases of Inherited Disease, (77) 11:2443-2464 (1995).
Barton, N.W. et al. "Therapeutic response to intravenous infusions of glucocerebrosidase in a patient with Gaucher disease", Proc. Nat!. Acad. Sci, 87:1913-1916 (Mar. 1990).
Lauer, R.M. "Administration of a Mixture of Fungal Glucosidases to a Patient with Type II Glycogenosis (Pompe's Disease)", Pediatrics, 42:672-676 (1968).
Van den Hout., et al., "Enzyme therapy for Pompe disease with recombinant human exglucosidase from rabbit milk", J Inherit. Metab. Dis., 24:266-274 (2001).

(56) References Cited

OTHER PUBLICATIONS

Williams, J.C., et al., "Enzyme Replacement in Pompe Disease With an alpha-Glucosidase-Low Density Lipoprotein Complex", Birth Defects: Original Article Series, 16(1 ):415-423 (1980).

Yang, H.W. et al., "Recombinant Human Acid alpha-Glucosidase Corrects Acid alpha-Glucosidase—Deficient Human Fibroblasts, Quail Fibroblasts, and Quail Myoblasts", Pediatric Research, 43(3):374-380 (1998).

Amalfitano, A., et al., "Recombinant human acid a-glucosidase enzyme therapy for infantile glycogen storage disease type II: Results of a phase I/II clinical trial", Genetic in Medicine, 3(2):132-138 (2001).

Ausems, M., et al., "Frequency of glycogen storage disease type II in the Netherlands: implications for diagnosis and genetic counselling", European Journal of Human Genetics, 7:713-716 (1999).

Bijvoet, A.G.A., et al., "Recombinant human acid a-glucosidase: high level production in mouse milk, biochemical characteristics, correction of enzyme deficiency in GSDII KO mice", Human Molecular Genetics, 7(11):1815-1824 (1998).

Bijvoet, A.G.A., et al., "Human acid alpa-glucosidase from rabbit milk has therapeutic effect in mice with glycogen storage disease type II", Human Molecular Genetics, 8(12):2145-2153 (1999).

Brooks, D.A., "Immune Response to Enzyme Replacement Therapy in Lysosomal Storage Disorder Patients and Animal Models", Molecular Genetics and Metabolism, 68:268-275 (1999).

De Barsy, T., et al., "Enzyme Replacement in Pompe Disease: An Attempt with Purified Human Acid alpha-Glucosidase", Birth Defects: Original Article Series, 9(2): 184-190 (1973).

Fuller, M., et al., "Isolation and characterisation of a recombinant, precursor form of lysosomal acid alpha-glucosidase", Eur. J Biochem, 234:903-909 (1995).

Hermans, M.M.P., et al., "The effect of a single base pair deletion (to T525) and a C1634T missense mutation (pro545leu) on the expression of lysosomal alpha-glucosidase in patients with glycogen storage disease type II", Human Molecular Genetics, 3(12):2213-2218 (1994).

Hermans, M.M.P., et al., "The conservative substitution Asp-645-+Glu in lysosomal alpha-glucosidase affects transport and phosphorylation of the enzyme in an adult patient with II glycogen-storage disease type II", Biochem. J, 289:687-693 (1993).

Hermans, M.M.P., et al., "Identification of a Point Mutation in the Human Lysosomal alpha-Glucosidase Gene Causing Infantile Glycogenosis Type II", Biochemical and Biophysical Research Communications, 179(2):919-926 (1991).

Hoefsloot, L.H., et al., "Characterization of the human lysosomal alpha-glucosidase gene", Biochem. J. 272:493-497 (1990).

Hug, G., et al., "Treatment Related Observations in Solid Tissues, Fibroblast Cultures and Amniotic Fluid Cells of Type II Glycogenosis, Hurler Disease and Metachromatic Leukodystrophy", Birth Defects: Original Articles Series, 9 (2):160-183 (1973).

Spellman et al., "Carbohydrate Structures of Human Tissue Plasminogen Activator Expressed in Chinese Hamster Ovary Cells," J. Bioi. Chem., 264(24):14100-14111 (Aug. 25, 1989). Exhibit 1070 in *BioMarin* v. *Duke University* IPR2013-00535, filed by BioMarin on Sep. 10, 2013.

P. D. Stahl, "The Macrophage Mannose Receptor: Current Status," Am. J. Respir. Cell Mol. Bioi., 2:317-318 (1990). Exhibit 2081 *BioMarin* v. *Duke University* IPR2013-00535, filed by Duke on May 22, 2014.

Stimson, "A Killer Yields to Modem Medicine," Quest 10(2) Mar./Apr. (2003). Exhibit C of the Appeal Brief filed Jan. 8, 2004 in the prosecution of the U.S. Pat. No. 7,056,712 Patent.

Stoll et al., "Mutant of Chinese hamster ovary cells with altered mannose 6-phosphate receptor activity is unable to synthesize mannosylphosphoryldolichol," Proc. Natl. Acad. Sci. USA 79:2296-2300 (1982).

Sun et al., "Enhanced response to enzyme replacement therapy in Pompe disease after the induction of immune tolerance," The American Journal of Human Genetics 81 :1042-1049 (2007).

Swaiman et al., "Late infantile acid maltase deficiency," Arch. Neural., 18:642 (1968). Exhibit 1023 in *BioMarin* v. *Duke University* IPR2013-00535, filed by BioMarin on Sep. 10, 2013.

Tonelli & Aitken, "New and emerging therapies for pulmonary complications of cystic fibrosis," Drugs 61 (10):1379-85 (2001).

Tong et al., "Ligand Interactions of the Cation-Independent Mannose 6-Phosphate Receptor," J. Biol. Chem., 264 (14):7962-69 (1989). Exhibit 2072 in *BioMarin* v. *Duke University* IPR2013-00535, filed by Duke on May 22, 2014.

Umpleby et al., "Protein turnover in acid maltase deficiency before and after treatment with a high protein diet," J. Neural. Neurosurg. Psychiatry, 50:587-92 (1987). Exhibit 2025 in *BioMarin* v. *Duke University* IPR2013-00535, filed by Duke on May 22, 2014.

Van der Ploeg et al., "Receptor-Mediated Uptake of Acid alpha-Glucosidase Corrects Lysosomal Glycogen Storage in Cultured Skeletal Muscle," Pediatric Research, 24(1 ):90-94 (1988). Exhibit 1014 in *BioMarin* v. *Duke University* IPR2013-00535, filed by BioMarin on Sep. 10, 2013.

Van der Ploeg et al., "Prospect for Enzyme Therapy in Glycogenosis II Variants: a Study on Cultured Muscle Cells," J. Neural. 235:392-96 (1988). Exhibit 2048 in *BioMarin* v. *Duke University* IPR2013-00535, filed by Duke on May 22, 2014.

Van der Ploeg et al., "Rat Heart Perfusion as Model System for Enzyme Replacement Therapy in Glycogenesis Type II," Pediatr. Res., 28:344-47 (1990). Exhibit 1064 in *BioMarin* v. *Duke University* IPR2013-00535, filed by BioMarin on Sep. 10, 2013.

Van Hove et al., "Purification of recombinant human precursor acid a-glucosidase," Biochemistry and Molecular Biology International, 43(3):613-623 (Oct. 1997). Exhibit 1007 in *BioMarin* v. *Duke University* IPR2013-00535, filed by BioMarin on Sep. 10, 2013.

Johan L. Van Hove, University of Colorado Anschutz Medical Campus, School of Medicine, Department of Pediatrics, http://www.ucdenver.edu/academics/colleges/medicalschool/departments/pediatrics/people/bios/Pages/vanhove, % 20johan.aspx. Exhibit 1114 in *BioMarin* v. *Duke University* IPR2013-00535, filed by BioMarin on Sep. 10, 2013.

Verity, "Infantile Pompe's Disease, Lipid Storage, and Partial Carnitine Deficiency," Muscle & Nerve 14:435-40 (1991). Exhibit 2059 in *BioMarin* v. *Duke University* IPR2013-00535, filed by Duke on May 22, 2014.

Walsh, G. and D. R. Headon, "Chapter 3-Downstream processing of protein products," Protein Biotechnology, Ed. Walsh, G. and D. R. Headon, West Sussex, John Wiley & Sons Ltd., 1994, 39-117. Exhibit 1092 in *BioMarin* v. *Duke University* IPR2013-00535, filed by BioMarin on Sep. 10, 2013.

Weinreb et al., "The lysosomal localization of sphingolipid hydrolases," Biochim Biophys Acta 159(1 ):141, (1968). Exhibit 1041 in *BioMarin* v. *Duke University* IPR2013-00535, filed by BioMarin on Sep. 10, 2013.

Wenk et al. "Quantitation of Mr 46000 and Mr 300000 mannose 6-phosphate receptors in human cells and tissues," Biochem. Int., 23(4):723-31 (1991). Exhibit 1056 in *BioMarin* v. *Duke University* I PR2013-00535, filed by BioMarin on Sep. 10, 2013.

Wisselaar et al., "Structural and Functional Changes of Lysosomal Acid alpha-Glucosidase during Intracellular Transport and Maturation," 268(3):2223-31 (1993). Exhibit 2045 in *BioMarin* v. *Duke University* IPR2013-00535, filed by Duke on May 22, 2014.

Wurm, F. M., "Production of Recombinant protein therapeutics in cultivated mammalian cells," Nature Biotechnology, 22(11 ):1393-1398 (2004). Exhibit 1069 in *BioMarin* v. *Duke University* IPR2013-00535, filed by BioMarin on Sep. 10, 2013.

Yasuda et al., "Human seminal deoxyribonuclease I (DNasel): purification, enzymological and immunological characterization and origin," Clinica Chimica Acta, 2:5-16 (1993). Exhibit 1101 in *BioMarin* v. *Duke University* IPR2013-00535, filed by BioMarin on Sep. 10, 2013.

Zellweger et al., "A mild form of muscular glycogenosis in two brothers with alpha-1,4-glucosidase deficiency," Ann. Pediatr. 205:413 (1965). Exhibit 1024 in *BioMarin* v. *Duke University* IPR2013-00535, filed by BioMarin on Sep. 10, 2013.

(56) References Cited

OTHER PUBLICATIONS

Zhao & Neufeld, "Purification and Characterization of Recombinant Human alpha-N-Acetylglucosaminidase Secreted by Chinese Hamster Ovary Cells," Protein Expression and Purification 19:202-211 (2000).
Transcript of the Deposition of Philip Green, dated Jun. 25, 2014 in *BioMarin v. Duke University* IPR2013-00535.
Genzyme Corporation Form 10-K for the fiscal year ended Dec. 31, 2010. Selected pages Exhibit 1144 in *BioMarin v. Duke University* IPR2013-00535, served by BioMarin on Jun. 25, 2014.
"$90M Payday at Duke" Triangle Business Journal Oct. 14, 2011. Exhibit 1147 in *BioMarin v. Duke University* IPR2013-00535, served by BioMarin on Jun. 25, 2014.
Duke University Financial Statements 2010/2011 Exhibit 1148 in *BioMarin v. Duke University* IPR2013-00535, served by BioMarin on Jun. 25, 2014.
"Myozyme alglucosidase alfa," Exhibit 1149 in *BioMarin v. Duke University* IPR2013-00535, served by BioMarin on Jun. 25, 2014.
Genzyme Corporation Form 10-K for the fiscal year ended Dec. 31, 2009. Selected pages. Exhibit 1150 in *BioMarin v. Duke University* IPR2013-00535, served by BioMarin on Jun. 25, 2014.
Genzyme Corporation Form 10-K for the fiscal year ended Dec. 31, 2009. Selected pages. Exhibit 1151 in *BioMarin v. Duke University* IPR2013-00535, served by BioMarin on Jun. 25, 2014.
Genzyme Corporation Form 10-K for the fiscal year ended Dec. 31, 2009. Selected pages. Exhibit 1152 in *BioMarin v. Duke University* IPR2013-00535, served by BioMarin on Jun. 25, 2014.
Extracts from EMEA approval for Myozyme. Exhibit B of Letter of Aug. 21, 2006 filed by Applicant Duke in the prosecution of the EPO Patent No. EP1301201 (Application No. 01951 000.7).
EPO's Notice of Intent to Grant a European Patent on the application No. 01951000.7, dated Oct. 27, 2006.
EPO's Decision to Grant a European Patent on the application No. 01951000.7, dated Feb. 1, 2007.
Opposition filed by Zystor Therapeutics, Inc. in the EPO Opposition Proceeding of Patent No. EP1301201 (Application No. 01951 000.7), dated Nov. 22, 2007.
Patentee's Reply to Opposition, dated Sep. 22, 2008, filed by Duke in the EPO Opposition Proceeding of Patent No. EP1301201 (Application No. 01951 000.7).
Patentee's Reply to Opposition, dated Dec. 7, 2010, filed by Duke in the EPO Opposition Proceeding of Patent No. EP1301201 (Application No. 01951 000.7).
Opponent's Observations in light of Patentee's Replies of Sep. 22, 2008, and Dec. 7, 2010, filed by Zystor on May 12, 2011 in the EPO Opposition Proceeding of Patent No. EP1301201 (Application No. 01951 000.7).
Patentee's reply of Jul. 29, 2011 filed by Duke in the EPO Opposition Proceeding of Patent No. EP1301201 Application No. 01951 000.7).
EPO Opposition Division's Facts and Submissions in Preparation to the Oral Proceedings, dated Jun. 8, 2012, entered in the EPO Opposition Proceeding of Patent No. EP1301201 Application No. 01951000.7).
Patentee's written submission, dated Oct. 11, 2012, filed by Duke in the EPO Opposition Proceeding of Patent No. EP1301201 (Application No. 01951 000.7).
ICH Topic E 11 Clinical Investigation of Medicinal Products in the Pediatric Population. European Medicines Agency (Jan. 2001).
Guidance for Industry E11 Clinical Investigation of Medicinal Products in the Pediatric Population (Dec. 2000).
Levine, "Ethics and regulation of clinical research," 2d Ed., (1986), excerpt Chapter 3, pp. 37 to 65.
Opponent's observations in light of the Opposition Division's Preliminary Opinion which accompanied the Summons of Jun. 8, 2012, filed by Zystor on Oct. 11, 2012 in the EPO Opposition Proceeding of Patent No. EP1301201 (Application No. 01951 000.7).
Opponent's observation of Nov. 28, 2012, filed in the EPO Opposition Proceeding of Patent No. EP1301201 (Application No. 01951 000.7).
Patentee's Letter of Dec. 11, 2012, filed in the EPO Opposition Proceeding of Patent No. EP1301201 (Application No. 01951000.7).
EPO Opposition Division's decision revoking European Patent No. EP1301201 Application No. 01951000.7), dated Feb. 1, 2013.
Patentee's Notice of Appeal in European Patent No. EP1301201 (Application No. 01951 000.7), filed by Duke and dated Apr. 9, 2013.
Patentee's Grounds of Appeal European Patent No. EP1301201 (Application No. 01951 000.7), filed by Duke and dated Jun. 10, 2013.
Jenkins et al., "Getting the glycosylation right: implications for the biotechnology industry," Nature Biotechnology 14:975-981 (1996).
Kakkis et al., "Overexpression of the Human Lysosomal Enzyme a-L-Iduronidase in Chinese Hamster Ovary Cells," Protein Expression and Purification, 5:225-32 (1994). Exhibit 1112 in *BioMarin v. Duke University* IPR2013-00535, filed by BioMarin on Sep. 10, 2013.
Kaplan et al., "Phosphohexosyl components of a lysosomal enzyme are recognized by pinocytosis receptors on human fibroblasts," Proc. Natl. Acad. Sci. USA, 74(5):2026-2030 (1977). Exhibit 1047 in *BioMarin v. Duke University* PR2013-00535, filed by BioMarin on Sep. 10, 2013.
Kawasaki et al., "Isolation and characterization of an avian hepatic binding protein specific for N-acetylglucosamine-terminated glycoproteins," J. Bioi. Chem. 252:6536-6543 (1977).
Kiss et al., "Practicing Safe Cell Culture: Applied Process Designs for Minimizing Virus Contamination Risk," PDA J. Pharma. Sci. and Tech., 65:715-29 (2011 ). Exhibit 1113 in *BioMarin v. Duke University* IPR2013-00535, filed by BioMarin on Sep. 10, 2013.
Kornfeld, "Trafficking of lysosomal enzymes," FASEB J. 1 :462-468 (1987).
R. Kornfeld and S. Kornfeld, "Comparative Aspects of Glycoprotein Structure," Annu. Rev. Biochem., 45:217-238 (1976). Exhibit 2082 in *BioMarin v. Duke University* IPR2013-00535, filed by Duke on May 22, 2014.
Kunita et al., "Molecular cloning of acid a-glucosidase eDNA of Japanese quail (*Cotumix cotumix* japonica) and the lack of its mRNA in acid maltase deficient quails," Biochimica et Biophysica Acta 1362:269-278 (1998).
Lin et al. "Cloning and expression of the human erythropoietin gene," Proc. Natl. Acad. Sci. USA, 82:7580-84 (1995). Exhibit 1108 *BioMarin v. Duke University* IPR2013-00535, filed by BioMarin on Sep. 10, 2013.
Lubiniecki et al., "Process Validation for Cell Culture-Derived Pharmaceutical Proteins," Large-Scale Mammalian Cell Culture Technology, Ed. A. S. Lubiniecki, New York, Marcel Dekker, Inc., 1990, 515-541 Exhibit 1090 in *BioMarin v. Duke University* IPR2013-00535, filed by BioMarin on Sep. 10, 2013.
Lunney & Ashwell, "A hepatic receptor of avian origin capable of binding specifically modified glycoproteins," Proc. Nat. Acad. Sci. USA 73:341-343 (1976).
Margolis & Hill, "Acid Maltase Deficiency in an Adult," Am. Rev. Respir. Dis. 134(2):328-31 (1986). Exhibit 2026 in *BioMarin v. Duke University* IPR2013-00535, filed by Duke on May 22, 2014.
Marian, M. and S. Baughman, "Recombinant Human Deoxribonuclease," Pharmaceutical Biotechnology, Ed. D. J. A. Crommelin and R. D. Sindelar, Amsterdam, Harwood Academic Publishers, 1997, 307-314. Exhibit 1073 in *BioMarin v. Duke University* 219 IPR2013-00535, filed by BioMarin on Sep. 10, 2013.
Matalon et al., "Hurler's syndrome, an a-Liduronidase deficiency," Biochem. Biophys. Res. Commun., 47(4):959-64 (1972). Exhibit 1042 in *BioMarin v. Duke University* IPR2013-00535, filed by BioMarin on Sep. 10, 2013.
McVie-Wylie, et al., "Biochemical and pharmacological characterization of different recombinant acid a-glucosidase preparations evaluated for the treatment of Pompe disease," Molecular Genetics & Metabolism 94:448-455 (2008).

(56) References Cited

OTHER PUBLICATIONS

McVie-Wylie et al., "An in Vivo Comparison of the Efficacy of Acid a-Glucosidase Produced in CHO Cells and Transgenic Rabbits," (2003). Exhibit 2047 in *BioMarin v. Duke University* IPR2013-00535, filed by Duke on May 22, 2014.

McVie-Wylie et al., "Multiple muscles in the MAD quail can be 'cross-corrected' of pathological glycogen accumulation after intravenous injection of an [E1-,polymerase-] adenovirus vector encoding human acid-a-glucosidase," J. Gene. Med. 5:399-406 (2003).

Mistry et al., "Therapeutic delivery of proteins to macrophages: Implications for treatment of Gaucher's disease," The Lancet, 348:1555-1559 (1996). Exhibits 1058 and 2027 in *BioMarin v. Duke University* IPR2013-00535, filed by BioMarin on Sep. 10, 2013.

Modi, N. G., "Recombinant Tissue-Type Plasminogen Activator and Factor VIII," Pharmaceutical Biotechnology, Ed. D. J. A. Crommelin and R. D. Sindelar, Amsterdam, Harwood Academic Publishers, 1997, 297-306. Exhibit 1072 in *BioMarin v. Duke University* IPR2013-00535, filed by BioMarin on Sep. 10, 2013.

Morell et al., "Chemistry and Metabolism of Macromolecules: Physical and Chemical Studies on Ceruloplasmin: V. Metabolic Studies on Sialic Acid-Free Ceruloplasmin In Vivo," J. Bioi. Chem., 243:155-59 (1968). Exhibit 2041 in *BioMarin v. Duke University* 226 IPR2013-00535, filed by Duke on May 22, 2014.

Mutsaers et al., "Determination of the Structure of the Carbohydrate Chains of Acid a—Glucosidase from Human Placenta," Biochim. Biophys. Acta, 911 :244-51 (1987). Exhibit 2037 in *BioMarin v. Duke University* IPR2013-00535, filed by Duke on May 22, 2014.

Noguchi et al., "Immunogenicity of N-glycolylneuraminic Acid-Containing carbohydrate chains of recombinant human erythropoietin expressed in Chinese hamster ovary cells," J. Biochem. 117:59-62 (1995).

Ogawara et al., "Pharmacokinetic Evaluation of Mannosylated Bovine Serum Albumin as a Liver Cell-Specific Carrier: Quantitative Comparison with Other Hepatotropic Ligans," J. Drug Targeting, 6(5):349-60 (1999). Exhibit 2039 in *BioMarin v. Duke University* IPR2013-00535, filed by Duke on May 22, 2014.

Olijve et al., "Molecular biology and biochemistry of human recombinant follicle stimulating hormone (Puregon)," Molecular Human Reproduction, 2(5):371-382 (1996). Exhibit 1102 in *BioMarin v. Duke University* IPR2013-00535, filed by BioMarin on Sep. 10, 2013.

Otter et al., "Mechanisms of Tissue-type Plasminogen Activator (tPA) Clearance by the Liver," Annals New York Academy of Sciences, 431-442 (1992). Exhibit 1083 in *BioMarin v. Duke University* I PR2013-00535, filed by BioMarin on Sep. 10, 2013.

Ozturk, S. S., "Cell Culture Technology—An Overview," Cell Culture Technology for Pharmaceutical and Cell-Based Therapies, Ed. S. S. Ozturk and W.-S. Hu, Boca Raton, CRC Press 2006, 1-13. Exhibit 1076 in *BioMarin v. Duke University* IPR2013-00535, filed by BioMarin on Sep. 10, 2013.

Pastores et al., "Enzyme Therapy in Gaucher Disease Type 1: Dosage Efficacy and Adverse Effects in 33 Patients Treated for 6 to 24 Months," Blood, 82:408-416 (1993). Exhibit 1057 in *BioMarin v. Duke University* IPR2013-00535, filed by BioMarin on Sep. 10, 2013.

Pastores & Hughes, "Enzyme-replacement therapy for Pompe disease," Pediatr. Health, 3(1):41-49 (2009). Exhibit 2018 in *BioMarin v. Duke University* IPR2013-00535, filed by Duke on May 22, 2014.

Pavlou & Reichert, "Recombinant protein therapeutics—success rates, market trends and 235 values to 201 0," Nature Biotechnology 22:1513-1519 (2004).

"PDA 2005": "Process validation of protein manufacturing," PDA Journal of Pharmaceutical Science and Technology, Technical Report No. 42, Supplement, 59:1-28 (2005). Exhibit 1091 in *BioMarin v. Duke University* IPR2013-00535, filed by BioMarin on Sep. 10, 2013.

Pompe, "Over idiopatische hypertrophie van het hart," Ned Tijdschr Geneeskd 76:304 (1932). Exhibit 1010 in *BioMarin v. Duke University* IPR2013-00535, filed by BioMarin on Sep. 10, 2013.

Purchio et al., "Identification of mannose 6-phosphate in two asparagine-linked sugar chains of recombinant transforming growth factors-131 precursor," J. Bioi. Chem. 263:14211-14215 (1988).

Reichel, C. and G. Gmeiner, "Erythropoietin and Analogs," Handbook of Experimental Pharmacology, Eds. D. Thieme and P. Hemmersbach, Berlin Heidelberg, Springer-Verlag 2010, 252-294 (201 0). Exhibit 1106 in *BioMarin v. Duke University* IPR2013-00535, filed by BioMarin on Sep. 10, 2013.

Reuser et al., "Uptake and Stability of Human and Bovine Acid—Glucosidase in Cultured Fibroblasts and Skeletal Muscle Cells from Glycogenosis Type II Patients," Exp. Cell Res. 155:178-89 (1984). Exhibit 2046 in *BioMarin v. Duke University* IPR2013-00535, filed by Duke on May 22, 2014.

Reuser et al., "Defects in synthesis, phosphorylation, and maturation of acid a-glucosidase in glycogenosis type II," J. Bioi. Chem. 260:8336-8341 (1985).

Reuser et al, "Giycogenosis Type II (Acid Maltase Deficiency)," Muscle and Nerve, Suppl. 3: S61-S69 (1995). Exhibit 1039 in *BioMarin v. Duke University* IPR2013-00535, filed by BioMarin on Sep. 10, 2013.

Reuser et al., "Enzyme Therapy for Pompe Disease: from Science to Industrial Enterprise," Eur. J. Pediatr. 161 :S1 06-S111 (2002). Exhibit 2049 in *BioMarin v. Duke University* IPR2013-00535, filed by Duke on May 22, 2014.

Richards et al., "Antibody response in patients with Gaucher disease after repeated infusion with macrophage-targeted glucocerebrosidase," Blood, 82(5):1402-09 (1993). Exhibit 1060 in *BioMarin v. Duke University* IPR2013-00535, filed by BioMarin on Sep. 10, 2013.

Rose and Stotter, "ICH E 11: Clinical investigation of medicinal products in paediatric population," in Guide to Paediatric Clinical Research (Rose and van den Anker eds. 2007) excerpt p. 33.

Rosenberg et al., "Immunosurveillance of alglucerase enzyme therapy for Gaucher patients: induction of humoral tolerance in seroconverted patients after repeat administration," Blood, 93(6):2081-88 (1999). Exhibit 1061 in *BioMarin v. Duke University* IPR2013-00535, filed by BioMarin on Sep. 10, 2013.

Ryff et al., "Interferons and Interleukinds," Pharmaceutical Biotechnology Fundamentals and Applications, Ed. D. J. A. Crommelin, R. D. Sindelar, B. Meibohm, London, Informa Healthcare 2008, 243-264. Exhibit 1075 in *BioMarin v. Duke University* IPR2013-00535, filed by BioMarin on Sep. 10, 2013.

Sando, G. N. and E F. Neufeld, "Recognition and Receptor-Mediated Uptake of a Lysosomal Enzyme, alpha-Iduronidase, by cultured Human Fibroblasts," Cell, 12:619-627 (1977). Exhibit 1048 in *BioMarin v. Duke University* IPR2013-00535, filed by BioMarin on Sep. 10, 2013.

Santell et al., "Aberrant Metabolic Sialylation of Recombinant Proteins Expressed in Chinese Hamster Ovary Cells in High Productivity Cultures," Biochem. and Biophys. Res. Commun., 258:132-37 (1999). Exhibit 2044 in *BioMarin v. Duke University* IPR2013-00535, filed by Duke on May 22, 2014.

Sarnat, et al., "Lipid Storage Myopathy in Infantile Pompe Disease," Arch. Neural. 39:180-183 (1982). Exhibit 2057 in *BioMarin v. Duke University* IPR2013-00535, filed by Duke on May 22, 2014.

Selak et al., "Mitochondrial Activity in Pompe's Disease," Pediatr. Neural. 23:54-57 (2000). Exhibit 2058 in *BioMarin v. Duke University* IPR2013-00535, filed by Duke on May 22, 2014.

Shak, S., "Aerosolized Recombinant Human DNase I for the Treatment of Cystic Fibrosis," Chest, 107(2):65S-70S (Feb. 1995). Exhibit 1080 in *BioMarin v. Duke University* IPR2013-00535, filed by BioMarin on Sep. 10, 2013.

Shak et al., "Recombinant human DNase I reduces the viscosity of cystic fibrosis sputum," Proc. Natl. Acad. Sci. USA,87:9188-9192 (Dec. 1990). Exhibit 1074 in *BioMarin v. Duke University* I PR2013-00535, filed by BioMarin on Sep. 10, 2013.

Shen et al., "Recombinant DNA Technology and Cell Line Development," Cell Culture Technology for Pharmaceutical and Cell-Based Therapies, Ed. S. S. Ozturk and W.-S. Hu, New York, Taylor & Francis 2006, 15-40. Exhibit 1104 in *BioMarin v. Duke University* IPR2013-00535, filed by BioMarin on Sep. 10, 2013.

Slonim et al., "Identification of two subtypes of infantile acid maltase deficiency," Journal of Pediatrics, 137(2):283-285 (2000).

(56) References Cited

OTHER PUBLICATIONS

Smith et al., "Muscular form of glycogenosis type II (Pompe)," Neurology, 17:537 (1967). Exhibit 1022 in *BioMarin v. Duke University* IPR2013-00535, filed by BioMarin on Sep. 10, 2013.
Kikuchi, T., et al., "Clinical and Metabolic Correction of Pompe Disease by Enzyme Therapy in Acid Maltase-deficient Quail", J Clin. Invest., 101(4):827-833 (1998).
Martiniuk, F., et al., "Recombinant Human Acid alpha-Glucosidase Generated in Bacteria: Antigenic, but Enzymatically Inactive", DNA and Cell Biology, 11(9):701-706 (1992).
Reuser, A.J.J., et al., "Biochemical, Immunological, and Cell Genetic Studies in Glycogenosis Type II", Am J Hum Genet, 30:132-143 (1978).
Slonim, A.E., et al., "Improvement of muscle function in acid maltase deficiency by high-protein therapy", Neurology, 33:34-38 (1983).
Van der Ploeg, A.T., et al., "Intravenous Administration of Phosphorylated Acid alpha-Glucosidase Leads to Uptake of Enzyme in Heart and Skeletal Muscle of Mice", J. Clin. Invest., 87:513-518 (1991).
Wu, J-Y., et al., "Expression of Catalytically Active Human Multifunctional Glycogen—De branching Enzyme and Lysosomal Acid Alpha-Glucosidase in Insect Cells", Biochemistry and Molecular Biology International, 39(4):755-764 (1996).
Watson J G. et al., "Bone Marrow Transplantation for Glycogen Storage Disease Type II (Pompe's Disease)", N. Eng. J Med., 314:385 (1986).
Martiniuk, F., et al., "Carrier Frequency for Glycogen Storage Disease Type II in New York and Estimates of Affected Individuals Born With the Disease", American Journal of Medical Genetics, 76:69-72 (1998).
Schiffmmm R., .et al., "Infusion of alpha-galactosidase A reduces tissue globotriaosylceramide storage in patients with Fabry disease", Proc. Natl. Acad. Sci., 97(1):365-370 (2000).
Van Hove, J.L.K, et al., "High-level production of recombinant human lysosomal acid alpha-glucosidase in Chinese hamster ovary cells which targets to heart muscle and corrects glycogen accumulation in fibroblasts from patients with Pompe disease", Proc. Natl. A cad. Sci., 93:65-70 (1996).
Lei, K.J ., et al. "Genetic Basis of Glycogen Storage Disease Type 1a: Prevalent Mutations at the Glucose-6-Phosphatase Locus", Am. J. Hum. Gen., 57( 4):766-771 (1995).
Pauly, D.F., et al., "Complete correction of acid alpha-glucosidase deficiency in Pompe disease fibroblasts in vitro, and lysosomally targeted expression in neonatal rat cardiac and skeletal muscle", Gene Therapy, 5(4):473-480 (1998).
Chen, Y-T, et al., "Towards a molecular therapy for glycogen storage disease type II (Pompe disease)", Mol. Medicine Today, 6(6):245-251 (2000).
Kalckis, E., et al., "Recombinant alpha-L-iduronidase replacement therapy in mucopolysaccharidosis 1: Results of a human clinical trial", Am. J Hum. GeneL, 63(4):A25 (1998).
Byrne, B.J., et al., "Reconstitution of Acid alpha-glucosidase activity in a mouse model of cardioskeleton myopathy, Pompe's Disease", Circulation, 98(17):1737 (1998).
Bodamer et al., "Dietary Treatment in Late-Onset Acid Maltase Deficiency," Eur. J. Pediatr. 156 [Suppl.1]:S39-S42 (1997). Exhibit 2023 in *BioMarin v. Duke University* IPR2013-00535, filed by Duke on May 22, 2014.
Brady et al., "Replacement therapy for inherited enzyme deficiency. Use of purified ceramidetrihexosidase in Fabry's disease," N. Engl. J. Med., 289(1 ):9-13 (1973). Exhibit 1045 in *BioMarin v. Duke University* IPR2013-00535, filed by BioMarin on Sep. 10, 2013.
Brady et al., "Replacement therapy for inherited enzyme deficiency. Use of purified glucocerebrosidase in Gaucher's disease," N. Engl. J. Med., 291 (19):989-93 (1974). Exhibit 1050 in *BioMarin v. Duke University* IPR2013-00535, filed by BioMarin on Sep. 10, 2013.
Brady et al., "Enzyme replacement therapy for Gaucher disease: Critical Investigations beyond demonstration of clinical efficacy," Biochem. Med. Metab. Bioi., 52(1):1-9 (1994). Exhibit 1055 in *BioMarin v. Duke University* PR2013-00535, filed by BioMarin on Sep. 10, 2013.
Brady et al. "Management of Neutralizing Antibody to Ceredase in a Patient With Type 3 Gaucher Disease," Pediatrics, 100(6):e11 (1997). Exhibit 1012 in *BioMarin v. Duke University* IPR2013-00535, filed by BioMarin on Sep. 10, 2013.
Brown et al., "Process development for the production of recombinant antibodies using the glutamine synthetase (GS) system," Cytotechnology, 9:231-236 (1992). Exhibit 1077 in *BioMarin v. Duke University* IPR2013-00535, filed by BioMarin on Sep. 10, 2013.
Brunetti et al., "Herpes Simplex Virus Glycoprotein D Acquires Mannose 6-Phosphate Residues and Binds to Mannose 6-Phosphate Receptors," J. Biol. Chem. 269:17067-17074 (1994).
Buetler et al., "Enzyme replacement therapy in Gaucher's disease: Preliminary Clinical trial of a new enzyme preparation," Proc. Natl. Acad. Sci. USA, 74:10:4620-4623 (1997). Exhibit 1059 in *BioMarin v. Duke University* PR2013-00535, filed by BioMarin on Sep. 10, 2013.
Cacia et al., "Human DNase I contains Mannose 6-Phosphate and Binds the Cation-Independent Mannose 6-Phosphate Receptor," Biochemistry, 37:15154-61 (1988). Exhibit 1100 in *BioMarin v. Duke University* IPR2013-00535, filed by BioMarin on Sep. 10, 2013.
Cheresh et al., "A Monoclonal antibody recognizes an O-acylated sialic acid in a human melanoma-associated ganglioside," J. Biol. Chem. 259:7453-7459 (1984).
Cori, G.T. "Glycogen structure and enzyme deficiencies in glycogen storage disease," Harvey Lect, 8:145 (1954). Exhibit 1017 *BioMarin v. Duke University* IPR2013-00535, filed by BioMarin on Sep. 10, 2013.
Crocker & Farber, "Niemann-Pick Disease: A Review of Eighteen Patients," Medicine (Baltimore) 37(1 ):1-95 (1958). Exhibit 2030 in *BioMarin v. Duke University* IPR2013-00535, filed by Duke on May 22, 2014.
R. D. Cummings, "Synthesis of Asparagine-Linked Oligosaccharides: Pathways, Genetics, and Metabolic Regulation," Glycoconjugates: Composition, Structure and Function. New York: Marcel Dekker, 1992. Exhibit 2080 in *BioMarin v. Duke University* IPR2013-00535, filed by Duke on May 22, 2014.
R. D. Cummings, "Synthesis of Asparagine-Linked Oligosaccharides: Pathways, Genetics, and Metabolic Regulation," Glycoconjugates: Composition, Structure and Function. New York: Marcel Dekker, 1992.
Daugherty et al., "Study of cohort-specific consent and patient control in Phase I cancer trials," J. Clin. Oneal. 16 (7)2305-2312 (1998).
De Duve, C., "From cytases to lysosomes," Fed. Proc., 23:1045-49 (1964). Exhibit 1044 in *BioMarin v. Duke University* PR2013-00535, filed by BioMarin on Sep. 10, 2013.
De Leeuw, Renata, et al., Structure-function relationship of recombinant follicle stimulating hormone (Puregon), Molecular Human Reproduction 2(5):361-69 (1996). Exhibit 1107 in *BioMarin v. Duke University* IPR2013-00535, filed by BioMarin on Sep. 10, 2013.
Deutscher, S. L. and C. B. Hirschberg, "Mechanism of Galactosylation in the Goli Apparatus," J. Bioi. Chem., 261 (1 ):96-1 00 (Jan. 5, 1986). Exhibit 1086 in *BioMarin v. Duke University* I PR2013-00535, filed by BioMarin on Sep. 10, 2013.
DiCioccio et al., "Phosphorylation and subcellular location of alpha-L-fucosidase in lymphiod cells from patients with 1-cell disease and pseudo-Hurler polydystrophy," Glycobiology, 3(5):489-95 (1993). Exhibit 1099 in *BioMarin v. Duke University* IPR2013-00535, filed by BioMarin on Sep. 10, 2013.
Di Marco et al., "Bovine generalised glycogenosis type II. Uptake of lysosomal alpha-glucosidase by cultured skeletal muscle and reversal of glycogen accumulation," FEBS Lett., 190:301-04 (1985). Exhibit 1053 in *BioMarin v. Duke University* IPR2013-00535, filed by BioMarin on Sep. 10, 2013.
DiMasi et al., "Trends in risks associated with new drug development: success rates for investigational drugs," Clinical Pharmacology & Therapeutics 87(3):272-277 (2010).

(56) References Cited

OTHER PUBLICATIONS

DiMauro et al., "Mitochondrial Encephalomyopathies: Therapeutic Approaches," Neural. Sci., 21 :S901-08 (2000). Exhibit 2075 in *BioMarin* v. *Duke University* IPR2013-00535, filed by Duke on May 22, 2014.

Einarsson et al., "Large-scale purification of human tissue-type plasminogen activator using monoclonal antibodies," Biochimica et Biophysica Acta, 830:1-10 (1985). Exhibit 1071 in *BioMarin* v. *Duke University* IPR2013-00535, filed by BioMarin on Sep. 10, 2013.

Fernandes et al., "Glycogen Storage Disease: Recommendations for Treatment," Eur. J. Pediatr. 147:226-28 (1988). Exhibit 2076 in *BioMarin* v. *Duke University* IPR2013-00535, filed by Duke on May 22, 2014.

Fratantoni, J.C. and E F. Neufeld, "Hurler and Hunter Syndromes: Mutual correction of the defect in cultured fibroblasts," Science, 162(3853):570-72 (1968). Exhibit 1046 in *BioMarin* v. *Duke University* IPR2013-00535, filed by BioMarin on Sep. 10, 2013.

Friedman et al., "A Comparison of the Pharmacological Properties of Carbohydrate Remodeled Recombinant and Placental-Derived 13-Giucocerebrosidase: Implications for Clinical Efficacy in Treatment of Gaucher Disease," Blood, 93:2807-16 (1999). Exhibit 2040 in *BioMarin* v. *Duke University* IPR2013-00535, filed by Duke on May 22, 2014.

Fujita et al, "Japanese Quail and Human Acid Maltase Deficiency: A Comparative Study," Brain Dev., 13:247-255 (1991). Exhibit 1063 in *BioMarin* v. *Duke University* IPR2013-00535, filed by BioMarin on Sep. 10, 2013.

Funk et al., "Expression of the Insulin-Like Growth Factor-11/Mannose-6-Phosphate Receptor in Multiple Human Tissues during Fetal Life and Early Infancy," J. Clin. Endocrin. Metab., 75(2):424-31 (1992). Exhibit 2031 in *BioMarin* v. *Duke University* IPR2013-00535, filed by Duke on May 22, 2014.

Gosse et al., "Recombinant protein and therapeutic monoclonal antibody drug development in the United States from 1980 to 1994," Clinical Pharmacology & Therapeutics 60(6):608-618 (1996).

Grabowski et al., "Genetic heterogeneity in Gaucher disease: physicokinetic and immunologic studies of the residual enzyme in cultured fibroblasts from nonneuronopathic and neuronopathic patients," Am. J. Med. Genet. 21 (3):529-49 (1985). Exhibit 1043 in *BioMarin* v. *Duke University* IPR2013-00535, filed by BioMarin on Sep. 10, 2013.

Grabowski et al., "Enzyme therapy in type 1 Gaucher disease: comparative efficacy of mannose-terminated glucocerebrosidase from natural and recombinant sources," Ann. Intern. Med., 122(1):33-39 (1995). Exhibit 1052 in *BioMarin* v. *Duke University* IPR2013-00535, filed by BioMarin on Sep. 10, 2013.

Grabowski et al., "Enzyme therapy for Gaucher disease: the first 5 years," Blood Reviews, 12:115-133 (1998). Exhibit 1011 in *BioMarin* v. *Duke University* IPR2013-00535, filed by BioMarin on Sep. 10, 2013.

Harris et al., "Tissue Plasminogen Activator has an 0-Linked Fucose Attached to Theeonine-61 in the Epidermal Growth Factor Domain," Biochemistry, 30:2311-2314 (1991). Exhibit 1084 in *BioMarin* v. *Duke University* IPR2013-00535, filed by BioMarin on Sep. 10, 2013.

Hermans et al., "Human Lysosomal a-glucosidase: functional characterization of the glycosylation sites," Biochem. J., 289:681-86 (1993). Exhibit 2036 in *BioMarin* v. *Duke University* IPR2013-00535, filed by Duke on May 22, 2014.

Hers, H. G., "Alpha-glucosidase deficiency in generalized glycogen-storage disease (Pompe's disease)," Biochem. J., 86:11 (1963). Exhibit 1019 in *BioMarin* v. *Duke University* IPR2013-00535, filed by BioMarin on Sep. 10, 2013.

Hironaka et al., "Comparative study of the sugar chains of factor VIII purified from human plasma and from the culture media of recombinant baby hamster kidney cells," J. Bioi. Chem. 267:8012-8020 (1992). Exhibit 1081 in *BioMarin* v. *Duke University* IPR2013-00535, filed by BioMarin on Sep. 10, 2013.

Hitoshi et al., "A novel ganglioside, 9-0-acetyl GD1 b, is recognized by serum antibodies in Guillain-Barre syndrome," J. of Neuroimmunology 66:95-101 (1996).

Hoefsloot et al, "Primary structure and processing of lysosomal a-glucosidase; homology with the intestinal sucrose—isomaltase complex," The EMBO Journal, 7(6):1697-1704 (1988). Exhibit 1094 in *BioMarin* v. *Duke University* IPR2013-00535, filed by BioMarin on Sep. 10, 2013.

Hoefsloot et al., "Expression and routeing of human lysosomal aglucosidase in transiently transfected mammalian cells," Biochem. J., 272:485-492 (1990). Exhibit 1095 in *BioMarin* v. *Duke University* I PR2013-00535, filed by BioMarin on Sep. 10, 2013.

Hokke et al., "Sialylated carbohydrate chains of recombinant human glycoproteins expressed in Chinese hamster ovary cells contain traces of N-glycolyneuraminic acid," FEBS Lett. 275(2): 9-14 (1990).

Hokke et al., "Structural analysis of the sialylated N-and 0-linked carbohydrate chains of recombinant human erythropoietin expressed in Chinese hamster ovary cells. Silylation patterns and branch location of dimeric N-acetyllactosamine units," Euro. J. Biochem, 228:981-1008, 1995. Exhibit 1105 in *BioMarin* v. *Duke University* IPR2013-00535, filed by BioMarin on Sep. 10, 2013.

Hotchkiss et al., "The influence of carbohydrate structure on the clearance of recombinant tissue-type plasminogen activator," Thrombosis and Haemostasis, 60(2):255-261 (1988). Exhibit 1082 in *BioMarin* v. *Duke University* IPR2013-00535, filed by BioMarin on Sep. 10, 2013.

Howels, C. M., "Genetic engineering of human FSH (Gonai-F)," Human Reproduction Update, 2(2):172-91, 1996. Exhibit 1088 in. *BioMarin* v. *Duke University* IPR2013-00535, filed by BioMarin on Sep. 10, 2013.

Hu, W.-S., An advanced course in Cellular Bioprocess Technology, University of Minnesota, pp. 1-14 (Aug. 8-11, 2011 ). Exhibit 1067 in *BioMarin* v. *Duke University* IPR2013-00535, filed by BioMarin on Sep. 10, 2013.

Hubbard et al., "An Electron Microscope Autoradiographic Study of the Carbohydrate Recognition Systems in Rat Liver," J. Cell Bioi., 83:47-64 (1979). Exhibit 2042 in *BioMarin* v. *Duke University* IPR2013-00535, filed by Duke on May 22, 2014.

Hug et al., "Lysosomes in type II Glycogenosis," J. Cell Biol., 35(1):C1-6 (1967). Exhibit 1040 in *BioMarin* v. *Duke University* IPR2013-00535, filed by BioMarin on Sep. 10, 2013.

Ioannou et al., "Overexpression of Human a-Galactosidase A Results in Its Intracellular Aggregation, Crystallization in Lysosomes, and Selective Secretion," The Journal of Cell Biology, 119:1137-50 (1992). Exhibit 1111 in *BioMarin* v. *Duke University* IPR2013-00535, filed by BioMarin on Sep. 10, 2013.

Isaacs et al., "Acid Maltase Deficiency: a Case Study and Review of the Pathophysiological Changes and Proposed Therapeutic Measures," J. Neural. Neurosurg. Psychiatry, 49:1011-18 (1986). Exhibit 2028 in *BioMarin* v. *Duke University* IPR2013-00535, filed by Duke on May 22, 2014.

Jayapal et al., "Recombinant Protein Therapeutics from CHO Cells-20 Years and Counting," CHO Consortium, SBE Special Section, University of Minnesota, 40-47 (2007). Exhibit 1068 in *BioMarin* v. *Duke University* IPR2013-00535, fied by BioMarin on Sep. 10, 2013.

Ninomiya et al., "Demonstration of Acid alpha-Glucosidase in Different Types of Pompe Disease by Use of an immunochemical Method", Journal of Neurological Sciences, 66:129-139 (1984).

Lin et al., "Preparation of Monoclonal Antibodies Against Acid alpha-D-Glucosidase for Study of Chinese Gylcogenosis Yype II Patients", Hybridoma, 11(4):493-505 (1992).

Kishnani et al., "Cross-reactive immunologic material status affects treatment outcomes in Pompe disease infants", Molecular Genetics and Metabolism, 99:26-33 (2010).

U.S. Appl. No. 60/111,291, filed Dec. 7, 1998.

Declaration of Dr. Yuan-Tsong Chen dated Mar. 3, 2003, for United States Publication No. 2002-0110551.

Office action dated Jun. 14, 2002, for United States Publication No. 2002-0110551.

Response dated Sep. 16, 2002, for United States Publication No. 2002-0110551.

(56) References Cited

OTHER PUBLICATIONS

Decision by Board of Patent Appeals dated Jun. 17, 2005, for United States Publication No. 2002-0110551.
"Pharming Strengthened Partnership with Genzyme" Press release dated Aug. 1, 2000. Exhibit 1147 in *BioMarin* v. *Genzyme* IPR2013-00534.
"Pharming Successfully Completes the First Ever Phase II Study in Infantile Pompe's Disease" Press release dated Nov. 2, 1999. Exhibit 1147 in *BioMarin* v. *Genzyme* IPR2013-00534.
"The AGSD-UK (Association for Glycogen Storage Diseases-United Kingdom) Held Its Fifteenth Annual Conference" Press release dated Oct. 9, 1999. Exhibit 1147 in *BioMarin* v. *Genzyme* IPR2013-00534.
"Phase II Juvenile Trials Underway in the Netherlands Infantile Trials Continue" Press release dated Jul. 4, 1999. Exhibit 1147 in *BioMarin* v. *Genzyme* IPR2013-00534.
"Medical Team Rotterdam (NL) Satisfied with Progress in Pompe Disease Phase II Clinical Trials with Human Alpha-glucosidase", Press release dated Jun. 1, 1999. Exhibit 1147 in *BioMarin* v. *Genzyme* IPR2013-00534.
"Pharming Group NV. Reports Q1 Earnings 1999" Press release dated May 3, 1999. Exhibit 1147 in *BioMarin* v. *Genzyme* IPR2013-00534.
"Pharming and Genzyme Form Joint Venture to Develop Treatment for Pompe's Disease" Press release dated Oct. 14, 1998. Exhibit 1147 in *BioMarin* v. *Genzyme* IPR2013-00534.
"Genzyme, Pharming Announce Partnership to Develop Treatment for Pompe's Disease" Press release dated Jul. 14, 1998. Exhibit 1147 in *BioMarin* v. *Genzyme* IPR2013-00534.
"Excerpts from the Future of Biotechnology: Back to Nature" by George Hersback. Press release dated Oct. 5, 1997. Exhibit 1147 in *BioMarin* v. *Genzyme* IPR2013-00534.
Ponce et al. "Enzyme Therapy in Gaucher Disease Type 1: Effect of Neutralizing Antibodies to Acid beta-Giucosidase", Blood, 90(1):43-48 (1997).
Office Action for United States Publication No. 2003-0007963 dated Apr. 10, 2001.
Response filed in United States Publication No. 2003-0007963 dated Oct. 15, 2001.
Office Action for United States Publication No. 2003-0007963 dated Dec. 17, 2001.
Office Action for United States Publication No. 2003-0007963 dated Oct. 30, 2002.
Office Action for United States Publication No. 2004-0081645 dated Nov. 29, 2005.
Response filed in United States Publication No. 2004-0081645 dated Jun. 1, 2006.
Office Action for United States Publication No. 2004-0081645 dated Aug. 28, 2006.
Response filed in United States Publication No. 2004-0081645 dated Mar. 5, 2007.
Office Action for United States Publication No. 2004-0081645 dated May 29, 2007.
Response filed in United States Publication No. 2004-0081645 dated Aug. 31, 2007.
Interview summary record issued in United States Publication No. 2004-0081645 dated Nov. 8, 2007.
Notice of Allowability for United States Publication No. 2004-0081645 dated Nov. 8, 2007.
Pharming Press Release, "Phase I Trials Completed" dated Aug. 3, 1998.
Van den Haul et al., "Recombinant human alpha-glucosidase from rabbit milk in Pompe patients", The Lancet, 356:397-398 (2000).
Ding et al., "Long-Term Efficacy after [E1-, polymerase—] Adenovirus-Mediated Transfer of Human Acid-alpha-Glucosidase Gene Into Glycogen Storage Disease Type II Knockout Mice", Human Gene Therapy, 12:955-965 (2001).
Synpac Press Release (Jun. 1999) Duke University states clinical trials for Pompe's disease (cited in Opposition filed in connection with corresponding European Patent No. EP1301201).

Press Release (Apr. 2000) Genzyme General Obtains Rights to Pompe Disease Therapy from Synpac (cited in Opposition filed in connection with corresponding European Patent No. EP1301201).
CXVascular—New Products (VN29)-VASCULARNEWS "Nuvelo receives FDA fast track status for alfimeprase", Jun. 5, 2012 (http://www.cxvascular.corn).
Nagle, Mike "Three strikes for Bayer as alfimeprase trials fails", Dec. 13, 2006 (http://www.outsourcing-pharma.com).
Bell, Ed "Nastech Pharmaceutical Company Inc. and Procter & Gamble Announce Collaboration to Develop and Commercialize Parathyroid Hormone (PTH1-34) Nasal Spray for Treatment of Osteoporosis", P&G News, Nastech Pharmaceutical Company Inc., (Feb. 1, 2006).
The Life Sciences Blog-seattlepi, "Stories to watch: the comback companies" Aug. 26, 2008.
Matsuda, Ichiro "Mutant acid alpha-glucosidase in different types of glycogenesis type II", vol. 4, No. 7, 1985, pp. 590-592 (Japanese & English translation).
U.S. Patent Office, Patent Trial and Appeal Board, Final Written Opinion dated Feb. 23, 2015, Paper 86, U.S. Pat. No. 7,056,712 B2, Case IPR2013-00535 (*Biomarin Pharmaceuticals, Inc.* v. *Duke University*).
U.S. Patent Office, Patent Trial and Appeal Board, Final Written Opinion dated Feb. 23, 2015, Paper 81, U.S. Pat. No. 7,351,410, Case IPR2013-00534 (*Biomarin Pharmaceuticals, Inc.* v. *Genzyme Therapeutic Products Limited Partnership*).
U.S. Patent Office, Patent Trial and Appeal Board, Final Written Opinion dated Feb. 23, 2015, Paper 79, U.S. Pat. No. 7,655,226, Case IPR2013-00537 (*Biomarin Pharmaceuticals, Inc.* v. *Genzyme Therapeutic Products Limited Partnership*).
Joseph et al, "Immune tolerance induction to enzyme-replacement therapy by co-administration of short-term, low-dose methotrexate in a murine Pompe disease model", 2008 British Society for Immunology, Clinical and Experimental Immunology, 152:138-146.
Cousens et al, "Teaching tolerance—New approaches to enzyme replacement therapy for Pompe disease", Human Vaccines & Immunotherapeutics, Oct. 2012, vol. 8, Issue 10, pp. 1459-1464.
Extended European Search Report dated Sep. 9, 2014, issued in connection with European Patent Application No. 14 16 7882.1.
U.S. Appl. No. 09/454,711 van Bree et al. "Treatment of Pompe's Disease" filed (Dec. 6, 1999) BioMarin Pharmaceutical: Exhibit 1034, USPTO Case IPR2013-00535.
"Genzyme General Obtains Rights to Pompe Disease Therapy from Synpac Genzyme and Pharming to Fund Commercialization," Exhibit 1003 in *BioMarin* v. *Duke University* IPR2013-00535, filed by BioMarin on (Sep. 10, 2013).
Genzyme General Obtains Rights to Pompe Disease Therapy from Synpac Genzyme and Pharming to Fund Commercialization, Exhibit 1139 in *BioMarin* v. *Duke University* IPR2013-00535, served by BioMarin on (Apr. 21, 2014).
"Duke University Starts Clinical Trials for Pompe's Disease," Exhibit 1002 in *BioMarin* v. *Duke University* IPR2013-00535, filed by BioMarin on (Sep. 10, 2013).
"Duke University Starts Clinical Trials for Pompe's Disease," Exhibit 1128 in *BioMarin* v. *Duke University* IPR2013-00535, served by BioMarin on (Mar. 31, 2014).
"Duke University Starts Clinical Trials for Pompe's Disease," Exhibit 1140 in *BioMarin* v. *Duke University* IPR2013-00535, served by BioMarin on (Apr. 21, 2014).
"Genzyme General Obtains Rights to Pompe Disease Therapy from Synpac Genzyme and Pharming to Fund Commercialization," Proposed replacement of Exhibit 1003 in *BioMarin* v. *Duke University* IPR2013-00535, served by BioMarin on (Mar. 31, 2014).
"About EurekAlert!" Exhibit 1117 in *BioMarin* v. *Duke University* IPR2013-00535, served by BioMarin on (Mar. 31, 2014).
"EurekAlert!—Terms and Conditions," Exhibit 1118 in *BioMarin* v. *Duke University* IPR2013-00535, served by BioMarin on (Mar. 31, 2014).
"Pompe's Bulletin," Exhibit 1098 in *BioMarin* v. *Duke University* IPR2013-00535, filed by BioMarin on (Sep. 10, 2013).
"Pompe's Bulletin," Exhibit 1120 in *BioMarin* v. *Duke University* IPR2013-00535, served by BioMarin on Mar. 31, 2014.

(56) References Cited

OTHER PUBLICATIONS

"FDA issues 'orphan drug designation' to Netherlands company Pharming BV for medicine against Pompe's Disease," Exhibit 1096 in *BioMarin v. Duke University* IPR2013-00535, filed by BioMarin on Sep. 10, 2013.
"Duke obtains FDA designation for Pompe disease therapy," Exhibit 1018 in *BioMarin v. Duke University* IPR2013-00535, filed by BioMarin on Sep. 10, 2013.
"Market News," Exhibit 1129 in *BioMarin v. Duke University* IPR2013-00535, served by BioMarin on Mar. 31, 2014.
"Duke researchers develop first treatment for rare muscle disease," Exhibit 1013 in *BioMarin v. Duke University* IPR2013-00535, filed by BioMarin on Sep. 10, 2013.
"Phase II trials scheduled to begin," Exhibit 1065 in *BioMarin v. Duke University* IPR2013-00535, filed by BioMarin on Sep. 10, 2013.
"Phase II pilot trials begin in the Netherlands," Exhibit 1097 in *BioMarin v. Duke University* IPR2013-00535, filed by BioMarin on Sep. 10, 2013.
"Duke obtains FDA designation for Pompe disease therapy," Exhibit 1131 in *BioMarin v. Duke University* IPR2013-00535, filed by BioMarin on Apr. 4, 2014.
"Duke researchers develop first treatment for rare muscle disease," Exhibit 1122 in *BioMarin v. Duke University* IPR2013-00535, served by BioMarin on Mar. 31, 2014.
"Duke researchers develop first treatment for rare muscle disease," Exhibit 1126 in *BioMarin v. Duke University* IPR2013-00535, served by BioMarin on Mar. 31, 2014.
"Pompe disease therapy to be tested," Exhibit 1031 in *BioMarin v. Duke University* IPR2013-00535, filed by BioMarin on Sep. 10, 2013.
"Pompe disease therapy to be tested," Exhibit 1125 in *BioMarin v. Duke University* IPR2013-00535, served by BioMarin on (Mar. 31, 2014).
"Pharming's first Phase II clinical trial for Pompe's disease finalized, showing survival, skeletal muscle regeneration and overall improvement of heart and lung functions," Document D67 (Opponent's D51) filed by Opponent Zystor on Oct. 11, 2012 in the EPO Opposition Proceeding of Patent No. EP1301201 (Application No. 01951 000.7).
Acid Maltase Deficiency Association website pages, Exhibit 1135 in *BioMarin v. Duke University* IPR2013-00535, served by BioMarin on Mar. 31, 2014.
"General information- orphan drug designation," Exhibit 1119 in *BioMarin v. Duke University* IPR2013-00535, served by BioMarin on Mar. 31, 2014.
Acid Maltase Deficiency Association website pages, Exhibit 1116 in *BioMarin v. Duke University* IPR2013-00535, served by BioMarin on Mar. 31, 2014.
"Genzyme to acquire Novazyme Pharmaceuticals," Document D95 filed by Patentee Duke on Jun. 10, 2013 in the EPO Opposition Proceeding of Patent No. EP1301201 'Application No. 01951000.7).
"Genzyme and Pharming research agreement," Document D96 filed by Patentee Duke on Jun. 10, 2013 in the EPO Opposition Proceeding of Patent No. EP1301201 (Application No. 01951000.7).
LexisNexis document with headline "Duke to test new drug for children's disease," Exhibit 1121 in *BioMarin v. Duke University* IPR2013-00535, filed by BioMarin on (Apr. 4, 2014).
Acid Maltase Deficiency Association website pages, Exhibit 1123 in *BioMarin v. Duke University* IPR2013-00535, served by BioMarin on Mar. 31, 2014.
Acid Maltase Deficiency Association website pages, Exhibit 1124 in *BioMarin v. Duke University* IPR2013-00535, served by BioMarin on (Mar. 31,2014).
"General information on clinical trials," Exhibit 1130 in *BioMarin v. Duke University* IPR2013-00535, served by BioMarin on (Mar. 31, 2014).
"Duke researchers develop first treatment for rare muscle disease" and "Synpac sponsors research into Pompe disease," Document D38 filed by Opponent Zystor on May 12, 2011 in the EPO Opposition Proceeding of Patent No. EP1301201 (Application No. 01951 000.7).
"Comparison of 635 (GAAss-GAa) and 697 (IGF2ss-GAA) uptake into Rat L6 myoblasts," Document D41 filed by Opponent Zystor on May 12, 2011 in the EPO Opposition Proceeding of Patent No. EP1301201 (Application No. 01951 000.7).
"For Houma girl, Katrina's disruption a matter of life or death" at http://www.houmatoday.com/article/20050915/BREAKING/509150331 ?p=all&tc=pgall, as accessed on May 14, 2014. Exhibit 2050 in *BioMarin v. Duke University* IPR2013-00535, filed by Duke on May 22, 2014.
"150 attend first Innovation Council symposium; Chen honored for myozyme work" at http://insidedukemedicine.org/news/150-attendfirst-innovation-council-symposium-chenhonored-for-myozymework/, as accessed on May 14, 2014. Exhibit 2051 in *BioMarin v. Duke University* IPR2013-00535, filed by Duke on May 22, 2014.
"Fighting Pompe Disease," at http://www.ivanhoe.com/channels/p_printStory.cfm?storyid=29316, as accessed on May 14, 2014. Exhibit 2052 in *BioMarin v. Duke University* IPR2013-00535, filed by Duke on May 22, 2014.
"A Tale of Two Sisters: Treatment for Rare Genetic Disease Offers New Hope: Pompe Disease Affects About 10,000 People Worldwide" at http://abcnews.go.com/GMA/print?id=2074596, as accessed on May 14, 2014. Exhibit 2053 in *BioMarin v. Duke University* IPR2013-00535, filed by Duke on May 22, 2014.
"Distinguished Winners 1994-2007: James D. Watson Helix Awards Honor Biotech's Top Performers", at http://www.helixaward.com/helix_winners.html, as accessed on May 14, 2014. Exhibit 2054 in *BioMarin v. Duke University* IPR2013-00535, filed by Duke on May 22, 2014.
"Prix Galien—Committees: Galien Award abroad" at http://www.prixgalien.com/en/02/03/1 /united-kingdom.htm, as accessed on May 14, 2014. Exhibit 2055 in *BioMarin v. Duke University* IPR2013-00535, filed by Duke on May 22, 2014.
"Wonder drug helps Azaria tight killer muscle disease" at http://www.plymouth herald. co. u k/W al k-celebrate-10-years-wonderdrug-given-Azaria/story- 20986372-detail/story.html, as accessed on May 14, 2014. Exhibit 2056 in *BioMarin v. Duke University* IPR2013-00535, filed by Duke on May 22, 2014.
"$90M Payday at Duke" Triangle Business Journal Oct. 14, 2011, at http://www.bizjournals.com/triangle/print-edition/2011 /1 0/14/90mpayday-atduke. html?s=print, as accessed on May 16, 2014. Exhibit 2060 in *BioMarin v. Duke University* IPR2013-00535, filed by Duke on May 22, 2014.
Benzyme and Sanofi public filings as excerpted. Exhibit 2062 in *BioMarin v. Duke University* IPR2013-00535, filed by Duke on May 22, 2014.
Licensing Executive Society of Biopharmaceutical Deal Rates and Terms, Jun. 2008. Exhibit 2063 in *BioMarin v. Duke University* IPR2013-00535, filed by Duke on May 22, 2014.
Excerpts from Parr—Royalty Rates for Pharmaceuticals and Biotechnology—7th Edition, (IPRA, Yardley PA, 201 0). Exhibit 2066 in *BioMarin v. Duke University* IPR2013-00535, filed by Duke on May 22, 2014.
Edwards, "Biotechnology and Pharmaceutical Commercialization Alliances: Their structure and implications for University Technology Transfer Offices", in Intellectual Property Management in Health and Agriculture Innovation: A Handbook of Best Practices (eds. Ktrattiger, et al.) MIHR Oxford UK. Exhibit 2064 in *BioMarin v. Duke University* IPR2013-00535, filed by Duke on May 22, 2014.
"Myozyme becomes Lumizyme after biologics scale-up", In-Pharma Technologist.com, Feb. 16, 2009, accessed from http://www.inpharmatechnologist.com/contenVview/print/236301, as accessed on May 15, 2014. Exhibit 2067 in *BioMarin v. Duke University* IPR2013-00535, filed by Duke on May 22, 2014.
Myozyme (alglucosidase alfa) Prescribing Information. Exhibit 2068 in *BioMarin v. Duke University* IPR2013-00535, filed by Duke on May 22, 2014.
Lumizyme Prescribing Information. Exhibit 2069 in *BioMarin v. Duke University* IPR2013-00535, filed by Duke on May 22, 2014.
Technology Assignment Agreement. Exhibit 2070 in *BioMarin v. Duke University* IPR2013-00535, filed by Duke on May 22, 2014.

(56) References Cited

OTHER PUBLICATIONS

"Duke drug on verge of FDA nod," at http://www.heraldsun.com/tools/printfriendly.cfm?StoryiD=670448, as accessed on Nov. 21, 2005. Exhibit 2071 in *BioMarin v. Duke University* IPR2013-00535, filed by Duke on May 22, 2014.

Excerpts from Genzyme Form 10-K, Annual Report for the fiscal year ended Dec. 31, 2010, related to the number of patients. Exhibit 2073 in *BioMarin v. Duke University* IPR2013-00535, filed by Duke on May 22, 2014.

Excerpts from Genzyme Form 10-K, Annual Report for the fiscal year ended Dec. 31, 2010, related to royalty obligations in connection with Myozyme/Lumizyme. Exhibit 2074 in *BioMarin v. Duke University* IPR2013-00535, filed by Duke on May 22, 2014.

Duke University's Request for Rehearing Under 37 C.F.R. § 42.71(d). Paper 87 in *BioMarin v. Duke University* IPR2013-00535, filed by Duke on Mar. 25, 2015, pp. 1-12.

BioMarin Opposition to Duke University Request for Rehearing. Paper 88 in *BioMarin v. Duke University* IPR2013-00535, filed by BioMarin on Apr. 29, 2015, pp. 1-7.

Duke University's Reply in Support of its Request for Rehearing Under 37 C.F.R. § 42.71(d). Paper 89 in *BioMarin v. Duke University* IPR2013-00535, filed by Duke on May 4, 2015, pp. 1-9.

U.S. Patent Office, Patent Trial and Appeal Board, Decision on Request for Rehearing dated Jul. 14, 2015, Paper 90, U.S. Pat. No. 7,056,712 B2, *BioMarin v. Duke University* IPR2013-00535, pp. 1-21.

Duke University's Notice of Appeal. Paper 91 in *BioMarin v. Duke University* IPR2013-00535, filed by Duke on Sep. 11, 2015, pp. 1-10.

U.S. Patent Office, Patent Trial and Appeal Board, Supplemental Final Written Decision, Proceedings on Remand dated Jan. 17, 2018, Paper 92, U.S. Pat. No. 7,056,712 B2, *BioMarin v. Duke University* IPR2013-00535, pp. 1-24.

Duke University's Notice of Appeal. Paper 93 in *BioMarin v. Duke University* IPR2013-00535, filed by Duke on Mar. 19, 2018, pp. 1-29.

U.S. Court of Appeals for the Federal Circuit, Brief for Appellant in *Duke University v. Biomarin Pharmaceutical Inc.*, Appeal No. 2018-1696, IPR2013-0535, filed by Duke University on Sep. 24, 2018, pp. 1-118.

U.S. Court of Appeals for the Federal Circuit, Brief for Appellee in *Duke University v. BioMarin Pharmaceutical Inc.*, Appeal No. 2018-1696, IPR2013-0535, filed by BioMarin on Feb. 4, 2019, pp. 1-68.

U.S. Court of Appeals for the Federal Circuit, Reply Brief for Appellant in *Duke University v. Biomarin Pharmaceutical Inc.*, Appeal No. 2018-1696, IPR2013-0535, filed by Duke University on Apr. 26, 2019, pp. 1-41.

U.S. Court of Appeals for the Federal Circuit, Judgment, *Duke University v. Biomarin Pharmaceutical Inc.*, Appeal No. 2018-1696, IPR2013-0535, decided Oct. 11, 2019, pp. 1-2.

U.S. Court of Appeals for the Federal Circuit, Appellant's Petition for Rehearing En Banc in *Duke University v. Biomarin Pharmaceutical Inc.*, Appeal No. 2018-1696, IPR2013-0535, filed by Duke University on Dec. 11, 2019, pp. 1-30.

\* cited by examiner

TREATMENT OF GLYCOGEN STORAGE DISEASE TYPE II

This application is a continuation of U.S. application Ser. No. 15/066,211, filed on Mar. 10, 2016 (allowed), which is a continuation of U.S. application Ser. No. 14/485,071, filed Sep. 12, 2014 (issued as U.S. Pat. No. 9,370,556), which is a continuation of U.S. application Ser. No. 13/593,148, filed Aug. 23, 2012 (issued as U.S. Pat. No. 8,900,552), which is a continuation of U.S. application Ser. No. 13/064,556, filed Mar. 30, 2011 (abandoned), which is a continuation of U.S. application Ser. No. 12/604,267, filed Oct. 22, 2009 (abandoned), which is a continuation of U.S. application Ser. No. 11/889,457, filed Aug. 13, 2007 (abandoned), which is a continuation of U.S. application Ser. No. 11/039,281, filed Jan. 20, 2005 (abandoned), which is a continuation of U.S. application Ser. No. 09/902,461, filed Jul. 10, 2001 (issued as U.S. Pat. No. 7,056,712), which claims the benefit of U.S. Provisional Application No. 60/219,237, filed Jul. 18, 2000, the entire contents of each of which are hereby incorporated by reference in this application.

BACKGROUND OF THE INVENTION

Glycogen storage disease type II (GSD-II) (also known as Pompe disease or acid maltase deficiency) is a fatal genetic muscle disorder caused by a deficiency of acid α-glucosidase (GAA), a glycogen degrading lysosomal enzyme (Hirschhorn, R., "Glycogen storage disease type II: acid α-glucosidase (acid maltase) deficiency", in Scriver, C. R. et al., (eds) *The Metabolic and Molecular Basis of Inherited disease*, 7th Ed., McGraw-Hill, New York, 1995, pp. 2443-2464). The deficiency results in lysosomal glycogen accumulation in almost all tissues of the body, with cardiac and skeletal muscle being the most seriously affected. The combined incidence of all forms of GSD-II is estimated to be 1:40,000, and the disease affects all groups without an ethnic predilection (Martiniuk, F. et al., *Amer. J. Med. Genet.* 79:69-72 (1998); Ausems, M.G.E.M. et al., *Eur. J. Hum. Genet.* 7:713-716 (1999)).

Clinically, GSD-II encompasses a range of phenotypes differing as to age of onset, organs involved and clinical severity, generally correlating with the residual amount of GAA activity. In its most severe presentation (infantile GSD-II, or Pompe disease, in which less than 1% of normal GAA activity is present), infants are affected by a hypertrophic cardiomyopathy, generalized muscle weakness and hypotonia secondary to massive glycogen accumulation in cardiac and skeletal muscles (for review, see Hirschhorn, *supra*). The disease progresses rapidly, with death from cardiac failure usually occurring by 1 year of age. Juvenile (1-10% of normal GAA activity) and adult-onset (10-40% of normal GAA activity) forms of the disease are characterized by lack of severe cardiac involvement, later age of onset, and slower progression, but eventual respiratory or limb muscle involvement results in significant morbidity and mortality for the affected individuals.

Drug treatment strategies, dietary manipulations, and bone marrow transplantation have been employed as means for treatment for GSD-II, without significant success (Hug, G. et al., *Birth Defects Org. Ser.* 9:160-183 (1967); Slonim, A. E. et al., *Neurology* 33:34 (1983); Watson, J. G. et al., *N. Engl. J. Med.* 314:385 (1986)). Early attempts at enzyme replacement were also unsuccessful (Hug, G. and Schubert, W. K., *J. Clin. Invest.* 46:1073 (1967); de Barsy, T. et al., *Birth Defects Orig. Art. Ser.* 9:84-190 (1973); Williams, J. C. and Murray, A. K., "Enzyme replacement in Pompe disease with an alpha glucosidase low-density lipoprotein complex", in Desnick, R. J. (ed), *Enzyme Therapy in Genetic Diseases: 2*, New York, Alan R. Liss 1980; pp. 415-423)). A need remains for effective treatment of GSD-II.

SUMMARY OF THE INVENTION

The present invention is drawn to methods of treating glycogen storage disease type II (infantile, juvenile or adult-onset) in an individual, by administering to the individual a therapeutically effective amount of acid α-glucosidase (e.g., less than about 15 mg enzyme per kilogram of body weight, preferably about 1-10 mg enzyme per kilogram of body weight more preferably about 10 enzyme per kilogram of body weight or about 5 mg enzyme per kilogram of body weight), at a regular interval (e.g., monthly, bimonthly, weekly, twice weekly, daily). The acid α-glucosidase is human acid, α-glucosidase, preferably recombinant human acid α-glucosidase, more preferably, precursor form of human acid α-glucosidase, and even more preferably precursor form of human acid α-glucosidase produced in Chinese hamster ovary cells. The acid α-glucosidase is administered periodically (e.g., monthly, bimonthly, weekly, twice weekly, daily). In preferred embodiments, the acid α-glucosidase is administered intravenously; intramuscularly; intrathecally; or intraventricularly.

The methods of the invention provide the first effective means to treat an individual with glycogen storage disease type II.

DETAILED DESCRIPTION OF THE INVENTION

Figure 1A:
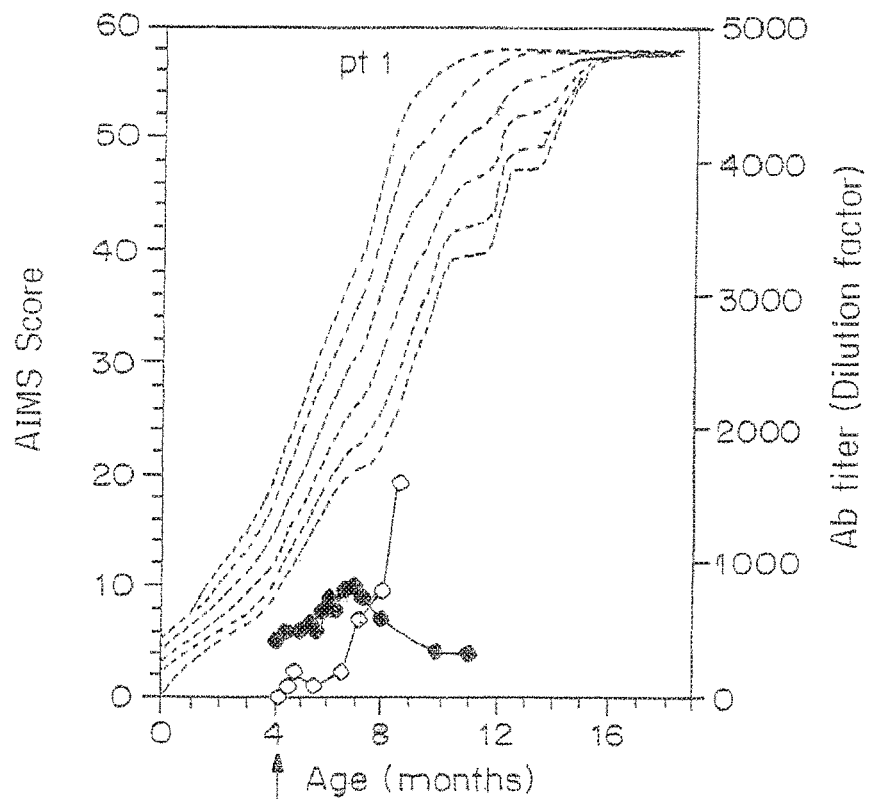
FIG. 1A-1C are a series of graphic representations depicting longitudinal data (for the first 16 months of age) on motor development as assessed by Alberta Infant Motor Scale (AIMS) (closed diamonds), and titer of antibodies to recombinant human acid α-glucosidase (rhGAA) (open diamonds) in three patients (patient 1, FIG. 1A; patient 2, FIG. 1B; patient 3, FIG. 1C) with infantile Pompe disease receiving enzyme replacement therapy. The arrow indicates when the enzyme therapy was initiated. AIMS scores in normal patients are plotted as dotted curves against age ($5^{th}$, $10^{th}$, $25^{th}$, $50^{th}$, $75^{th}$ and $95^{th}$ percentile, from bottom to top).

The present invention is drawn to methods of treating glycogen storage disease type II (GSD-II) in an individual, by administering the enzyme, acid α-glucosidase (GAA) to the individual, as well as the use of the enzyme, GAA, in the manufacture of a medicament for the treatment of glycogen storage disease type II. As described herein, Applicants have successfully treated infants suffering from GSD-II by administering GAA to the infants on a regular basis; the infants demonstrated improvement of cardiac status, pulmonary function, and neurodevelopment, as well as reduction of glycogen levels in tissue.

As a result of these findings, it is now possible for the first time to treat GSD-II, including infantile, juvenile and adult-onset GSD-II. Although the results described herein discuss individuals with the most severe form of GSD-II (infantile GSD-II), it is expected that the methods will be equally effective in individuals affected by juvenile or adult-onset GSD-II, and may, in fact, be even more effective, as individuals with juvenile or adult-onset GSD-II have higher levels of residual GAA activity (1-10%, or 10-40%, respectively), and therefore are likely to be more immunologically tolerant of the administered GAA (e.g., they are generally cross-reactive immunoreactive material (CRIM)-positive for endogenous GAA, so that their immune systems do not perceive the GAA as a "foreign" protein, and they do not develop anti-GAA antibodies). The enhanced efficacy in such individuals can be seen in patient 3, who was CRIM-positive and did not develop anti-GAA antibodies, and who demonstrated a normal progression of developmental milestones, in contrast with the variable course that was seen in CRIM-negative patients 1 and 2 (who did develop anti-GAA antibodies).

The terms, "treat" and "treatment," as used herein, refer to amelioration of one or more symptoms associated with the disease, prevention or delay of the onset of one or more symptoms of the disease, and/or lessening of the severity or frequency of one or more symptoms of the disease. For example, treatment can refer to improvement of cardiac status (e.g., increase of end-diastolic and/or end-systolic volumes, or reduction, amelioration or prevention of the progressive cardiomyopathy that is typically found in GSD-II) or of pulmonary function (e.g., increase in crying vital capacity over baseline capacity, and/or normalization of oxygen desaturation during crying); improvement in neurodevelopment and/or motor skills (e.g., increase in AIMS score); reduction of glycogen levels in tissue of the individual affected by the disease; or any combination of these effects. In one preferred embodiment, treatment includes improvement of cardiac status, particularly in reduction or prevention of GSD-II-associated cardiomyopathy. The terms, "improve," "increase" or "reduce," as used herein, indicate values that are relative to a baseline measurement, such as a measurement in the same individual prior to initiation of the treatment described herein, or a measurement in a control individual (or multiple control individuals) in the absence of the treatment described herein. A control individual is an individual afflicted with the same form of GSD-II (either infantile, juvenile or adult-onset) as the individual being treated, who is about the same age as the individual being treated (to ensure that the stages of the disease in the treated individual and the control individual(s) are comparable).

The individual being treated is an individual (fetus, child, adolescent, or adult human) having GSD-II (i.e., either infantile GSD-II, juvenile GSD-II, or adult-onset GSD-II). The individual can have residual GAA activity, or no measurable activity. For example, the individual having GSD-II can have GAA activity that is less than about 1% of normal GAA activity (infantile GSD-II), GAA activity that is about 1-10% of normal GAA activity (juvenile GSD-II), or GAA activity that is about 10-40% of normal GAA activity (adult GSD-II). The individual can be CRIM-positive or CRIM-negative for endogenous GAA. In a preferred embodiment, the individual is CRIM-positive for endogenous GAA. In another preferred embodiment, the individual is an individual who has been recently diagnosed with the disease. Early treatment (treatment commencing as soon as possible after diagnosis) is important for to minimize the effects of the disease and to maximize the benefits of treatment.

In the methods of the invention, human acid α-glucosidase (GAA) is administered to the individual. The GAA is in a form that, when administered, targets tissues such as the tissues affected by the disease (e.g., heart, muscle). In one preferred embodiment, the human GAA is administered in its precursor form, as the precursor contains motifs which allow efficient receptor-mediated uptake of GAA. Alternatively, a mature form of human GAA that has been modified to contain motifs to allow efficient uptake of GAA, can be administered. In a particularly preferred embodiment, the GAA is the precursor form of recombinant human GAA.

GAA is obtainable from a variety of sources. In a particularly preferred embodiment, recombinant human acid α-glucosidase (rhGAA) has been produced in Chinese hamster ovary (CHO) cell cultures is used (see, e.g., Fuller, M. et al., *Eur. J. Biochem.* 234:903-909 (1995); Van Hove, J. L. K. et al., *Proc. Natl. Acad. Sci. USA* 93:65-70 (1996); the entire teachings of these references are incorporated herein by reference). Production of GAA in CHO cells appears to yield a product having glycosylation which allows significant and efficient uptake of GAA in the desired tissues (heart and muscle); it is assumed that the glycosylation differs from that of GAA that is produced in transgenic mouse and rabbit milk (see, e.g., Bijvoet, A. G. A. et al., *Hum. Mol. Genet.* 7:1815-1824 (1998); Bijvoet, A. G. A. et al., *Hum. Mol. Genet.* 8:2145-2153 (1999)).

The GAA has a specific enzyme activity in the range of about 1.0-3.5 μmol/min/mg protein, preferably in the range of about 2-3.5 μmol/min/mg protein. In one preferred embodiment, the GAA has a specific enzyme activity of at least about 1.0 μmol/min/mg protein; more preferably, a specific enzyme activity of at least about 2.0 μmol/min/mg protein; even more preferably, a specific enzyme activity of at least about 2.5 μmol/min/mg protein; and still more preferably, a specific enzyme activity of at least about 2.75 μmol/min/mg protein.

GAA can be administered alone, or in compositions or medicaments comprising the GAA (e.g., in the manufacture of a medicament for the treatment of the disease), as described herein. The compositions can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

The GAA can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

GAA (or composition or medicament containing GAA) is administered by an appropriate route. In one embodiment, the GAA is administered intravenously. In other embodiments, GAA is administered by direct administration to a target tissue, such as heart or muscle (e.g., intramuscular), or nervous system (e.g., direct injection into the brain; intraventricularly; intrathecally). More than one route can be used concurrently, if desired.

GAA (or composition or medicament containing GAA) can be administered alone, or in conjunction with other agents, such as antihistamines (e.g., diphenhydramine) or immunosuppressants or other immunotherapeutic agents which counteract anti-GAA antibodies. The term, "in conjunction with," indicates that the agent is administered at about the same time as the GAA (or composition containing GAA). For example, the agent can be mixed into a composition containing GAA, and thereby administered contemporaneously with the GAA; alternatively, the agent can be administered contemporaneously, without mixing (e.g., by "piggybacking" delivery of the agent on the intravenous line by which the GAA is also administered, or vice versa). In another example, the agent can be administered separately (e.g., not admixed), but within a short time frame (e.g., within 24 hours) of administration of the GAA. In one preferred embodiment, if the individual is CRIM-negative for endogenous GAA, GAA (or composition containing GAA) is administered in conjunction with an immunosuppressive or immunotherapeutic regimen designed to reduce amounts of, or prevent production of, anti-GAA antibodies. For example, a protocol similar to those used in hemophilia patients (Nilsson, I. M. et al., *N. Engl. J. Med.* 318:947-50 (1988)) can be used to reduce anti-GAA antibodies. Such a regimen can also be used in individuals who are CRIM-positive for endogenous GAA but who have, or are at risk of having, anti-GAA antibodies. In a particularly preferred embodiment, the immunosuppressive or immunotherapeutic regimen is begun prior to the first administration of GAA, in order to minimize the possibility of production of anti-GAA antibodies.

GAA (or composition or medicament containing GAA) is administered in a therapeutically effective amount (i.e., a dosage amount that, when administered at regular intervals, is sufficient to treat the disease, such as by ameliorating symptoms associated with the disease, preventing or delaying the onset of the disease, and/or also lessening the severity or frequency of symptoms of the disease, as described above). The amount which will be therapeutically effective in the treatment the disease will depend on the nature and extent of the disease's effects, and can be determined by standard clinical techniques. In addition, in vitro or in vivo assays may optionally be employed to help identify optimal dosage ranges. The precise dose to be employed will also depend on the route of administration, and the seriousness of the disease, and should be decided according to the judgment of a practitioner and each patient's circumstances. Effective doses may be extrapolated from dose-response curves derived from in vitro or animal model test systems. In a preferred embodiment, the therapeutically effective amount is less than about 15 mg enzyme/kg body weight of the individual, preferably in the range of about 1-10 mg enzyme/kg body weight, and even more preferably about 10 mg enzyme/kg body weight or about 5 mg enzyme/kg body weight. The effective dose for a particular individual can be varied (e.g., increased or decreased) over time, depending on the needs of the individual. For example, in times of physical illness or stress, or if anti-GAA antibodies become present or increase, or if disease symptoms worsen, the amount can be increased.

The therapeutically effective amount of GAA (or composition or medicament containing GAA) is administered at regular intervals, depending on the nature and extent of the disease's effects, and on an ongoing basis. Administration at a "regular interval," as used herein, indicates that the therapeutically effective amount is administered periodically (as distinguished from a one-time dose). The interval can be determined by standard clinical techniques. In preferred embodiments, GAA is administered monthly, bimonthly; weekly; twice weekly; or daily. The administration interval for a single individual need not be a fixed interval, but can be varied over time, depending on the needs of the individual. For example, in times of physical illness or stress, if anti-GAA antibodies become present or increase, or if disease symptoms worsen, the interval between doses can be decreased.

In one preferred embodiment, a therapeutically effective amount of 10 mg enzyme/kg body weight is administered weekly. In another preferred embodiment, a therapeutically effective amount of 5 mg enzyme/kg body weight is administered twice weekly.

The invention additionally pertains to a pharmaceutical composition comprising human acid α-glucosidase, as described herein, in a container (e.g., a vial, bottle, bag for intravenous administration, syringe, etc.) with a label containing instructions for administration of the composition for treatment of glycogen storage disease type II, such as by the methods described herein.

The invention will be further and more specifically described by the following examples.

EXEMPLIFICATION

Phase I/II Trial of Use of Recombinant Human Acid α-Glucosidase

MATERIAL AND METHODS

Patients: Inclusion criteria were infants affected with infantile GSD-II having virtually absent GAA activity (<1% of normal in skin fibroblasts and/or muscle biopsy) and less than one year of age. Exclusion criteria included severe cardiorespiratory failure at baseline and/or other medical conditions likely to decrease survival. Because of the limited life expectancy of the disease following diagnosis, no placebo control was used. Historical control data indicated that virtually all patients died before 1 year of age (Table 1).

TABLE 1

Historical control data of infantile glycogen storage disease, type II

|  | Onset (months) | Death (months) | Length of disease course (months) |
|---|---|---|---|
| Duke University Medical Center (n = 30)* | | | |
| Mean ± SD | 5.1 ± 1.8 | 8.6 ± 2.4 | 3.5 ± 2.3 |
| Range | 2.4-10.3 | 3.3-12.4 | 0.0-9.0 |
| Slonim et al. (n = 10)** | | | |
| Mean ± SD | 2.5 ± 1.0 | 7.2 ± 2.8 | 4.7 ± 2.4 |
| Range | 1.0-4.0 | 4.0-12.0 | 2.0-9.0 |

*Data from Duke University Pompe Disease Registry
**Data from Slonim et al., *J. Pediatr.* 137: 283-285 (2000).

Three infants affected with infantile GSD-II as evidenced by reduced acid α-glucosidase activity to less than 1% of normal in skin fibroblasts and/or muscle biopsy were enrolled in the study. At the protein level, both patients 1 and 2 had no detectable GAA protein while patient 3 had reduced levels of GAA protein detected by immunoblot analysis. The baseline clinical data before the initiation of the therapy are summarized in Table 2.

with compression of the left main bronchus resulting in partial atelectasis of the left lung, and feeding difficulties and failure to thrive. Patients 2 and 3 were prenatally diagnosed with Pompe disease; importantly, each had a previous sibling that had died of symptoms typically attributable to the infantile GSD-II. Both patients had evidence of motor delays; in addition patient 2 had feeding difficulty, failure to thrive and severe cardiomyopathy.

Basic Design: The study was designed as a Phase I/II, open-label, single-dose, safety and efficacy study of rhGAA administered twice weekly in the 3 patients with infantile Pompe disease. The study was approved by the institutional review board, and parental written informed consent was obtained.

The study consisted of an initial Screening Phase, a 13-week Treatment Phase, and a Follow-up Treatment Phase. During the Screening Phase the initial clinical status of the patients was assessed; in addition, GAA and glycogen levels were determined in skeletal muscle biopsy samples. During the Treatment Phase, patients received intravenous infusions of rhGAA (5 mg/kg) twice weekly. Patients were closely monitored for any adverse responses to the enzyme infusions, as well as for any impact the rhGAA administrations had on the clinical progression of infantile GSD-II. General clinical assessments included routine physical examinations, supplemented by complete urine, hematological, and clinical chemistry analyses (electrolytes, glucose, creatinine, BUN, $CO_2$, protein, albumin, ALT, AST, bilirubin, alkaline phosphatase, CK and isozyme, uric acid). Exhaustive neurologic and motor function evaluations included manual muscle strength testing, Denver development testing, and AIMS (Alberta Infant Motor Scale; see Piper, M. C. and Darrah, J., *Motor Assessment of the Developing Infant*, WB Sanders Company, Philadelphia, 1994). Two-dimensional, M-mode and Doppler echocardiography were used to assess left ventricular mass, wall thickness and systolic as well as diastolic functions. Additionally, a variety of pulmonary functions (crying vital capacity, trend pulse-oximetry and end tidal carbon dioxide measurement, as well as negative inspiratory force maneuver) were monitored throughout the study. At the conclusion of the 13-week treatment phase, GAA activity, glycogen levels and histopathology of muscle biopsies obtained from

TABLE 2

Baseline Clinical Data on 3 Infantile Pompe Disease Patients

| Patient Number/Sex | Ethnic Background | Age rhGAA Started | Cardiac Status | Pulmonary Function | Motor Development (AIMS Score) | GAA Activity in Skin Fibroblasts (% of normal) | CRIM* Status | Current Age |
|---|---|---|---|---|---|---|---|---|
| Patient 1/male | Caucasian | 4 months | Severe cardiomyopathy; states post cardiac arrest | Borderline normal, left main bronchus compression due to markedly enlarged heart, $O_2$ desaturation | <<$5^{th}$ % | 0.84% | Negative | 29 months |
| Patient 2/male | African-American | 3 months | Moderate cardiomyopathy | $O_2$ desaturation during crying | <$5^{th}$ % | 0.57% | Negative | 25 months |
| Patient 3/male | Caucasian | 2½ months | Borderline cardiomyopathy | Normal | <<$5^{th}$ % | 0.69% | Positive | 23 months |

*CRIM = cross reactive immunoreactive material

Patient 1 presented at 2 months of age with cardiac arrest during elective surgical repair of an inguinal hernia. Subsequent evaluation when he was 4 months of age demonstrated evidence of severe hypotonia, with a motor development age estimated to be equivalent to that of a 3 week old. He also had profound cardiomyopathy and severe cardiomegaly the quadriceps muscles of the contra-lateral thigh of the pre-treatment biopsies were determined. The muscle biopsies were taken 3 days after the rhGAA infusion.

Enzyme source: rhGAA purified from the culture medium of rhGAA secreting CHO cells (Van Hove, J. L. K. et al., *Proc. Natl. Acad. Sci. USA* 93:65-70 (1996)) was provided as a GMP-grade, sterile and colorless solution by Synpac (North Carolina), Inc., 99 Alexander Drive, Suite NW20, Research Triangle Park, N.C. 27709. rhGAA was purified primarily as the 110-kD precursor protein with specific enzyme activity of 2.77-3.02 µmol/min/mg protein.

ELISA for anti-rhGAA antibodies: The ELISA for anti-rhGAA antibodies was a standard sandwich assay performed by Phoenix International Life Sciences, Inc. (Saint-Laurent, Quebec). Briefly, microtiter plates were coated with rhGAA at 2.0 µg/ml overnight and then blocked with bovine IgG. Patient serum, diluted to 1:100 and then serially diluted at 1:2, was reacted with the rhGAA on the plate. The amount of bound antibody was detected with a horseradish peroxidase conjugated goat anti-human secondary antibody and tetramethylbenzidine substrate by measuring the absorbances at 450 nm. Positive samples were defined as having an absorbance that was higher than the negative cutoff. This was defined as twice the A450 value of the normal human serum negative control. Titer was defined as the dilution of the serum that still had an A450 reading above the negative cutoff value.

GAA activity, glycogen content and Western blot analysis: GAA activity was assessed by measurement of 4-methyl-umbelliferyl-α-D-glucoside cleavage at pH 4.3 as previously described (Reuser, A. J. J. et al., *Am. J. Hum. Genet.* 30:132-143 (1978)). As an internal standard, acid-β-galactosidase activity was similarly assayed with the 4-methyl-umbilliferyl derivative as the substrate (Wenger, D. A. and Williams, C., "Screening for lysosomal disorders" in Hommes, F. A. (ed.), *Techniques in diagnostic human biochemical genetics: a laboratory manual*, Wiley-Liss, New York, 1991, pp. 587-617). Glycogen content was determined by treatment of tissue extracts with *A. niger* amyloglucosidase and measurement of glucose released (Van Hove, J. L. K. et al., *Proc. Natl. Acad. Sci. USA* 93:65-10 (1996)). Western blot analysis was performed with antibody raised in rabbits against purified placenta GAA (Van Hove, J. L. K. et al., *supra*).

Histology: One specimen of muscle was mounted on a chuck with gum tragacanth and quick-frozen in isopentane cooled by liquid nitrogen. Five micron sections were obtained and stained with hematoxylin and eosin, modified Gomori trichrome, ATPase at pH 4.35 and 9.4, nicotinamide dehydrogenase tetrazolium blue reductase, and phosphorylase. A second specimen was clamped in situ and placed in 2.5% glutaraldehyde. The tissue was processed without en bloc staining with uranyl acetate in order to avoid loss of glycogen. Semithin sections (0.5 micron) were stained with toluidine blue and thin sections stained with uranyl acetate and lead citrate and mounted on a copper grid for electron microscopy.

RESULTS

Patient Reaction to Treatment: The three patients with infantile Pompe disease received twice weekly intravenous infusions of rhGAA for 21-25 months. No serious allergic reactions occurred during enzyme therapy. However, three episodes of skin rash, accompanied by a mild fever and increased irritability occurred in two of the patients (patient 1 two episodes, patient 2 single episode). These symptoms resolved promptly after intravenous administration of diphenhydramine. After a second episode of skin rash, patient 1 was premedicated with oral diphenhydramine just prior to all subsequent rhGAA infusions, without further episodes. Patient 2 was similarly premedicated with oral diphenhydramine just prior to all subsequent infusions, without further episodes. Multiple hematological parameters, liver functions, renal functions, and urinalyses have all been in the normal range throughout the therapy period in all treated patients.

Figure 1B:
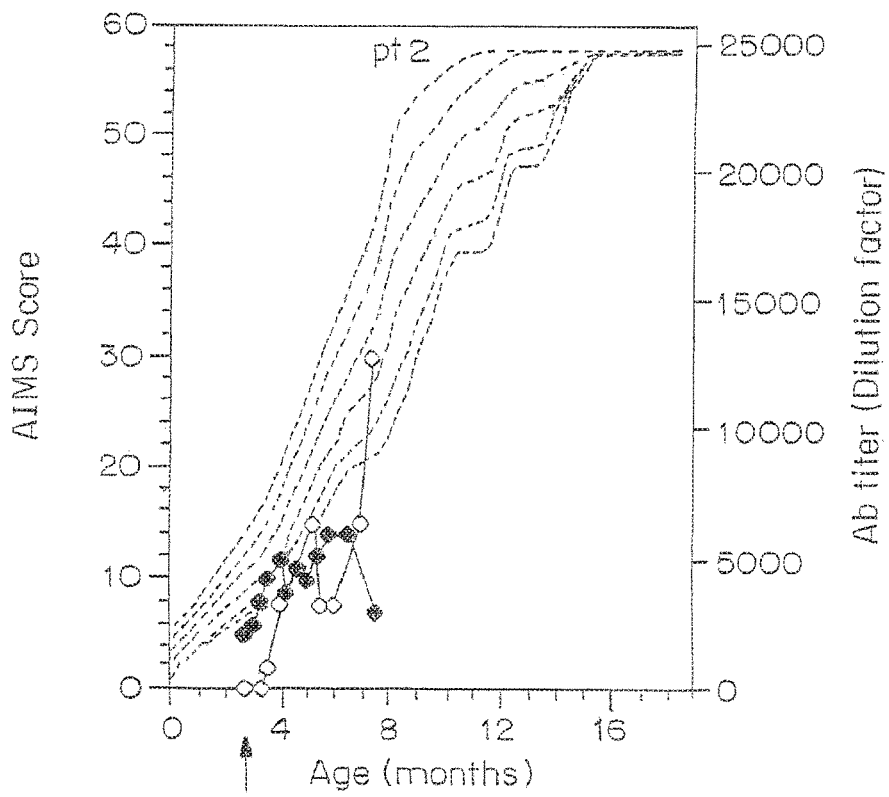
Figure 1C:
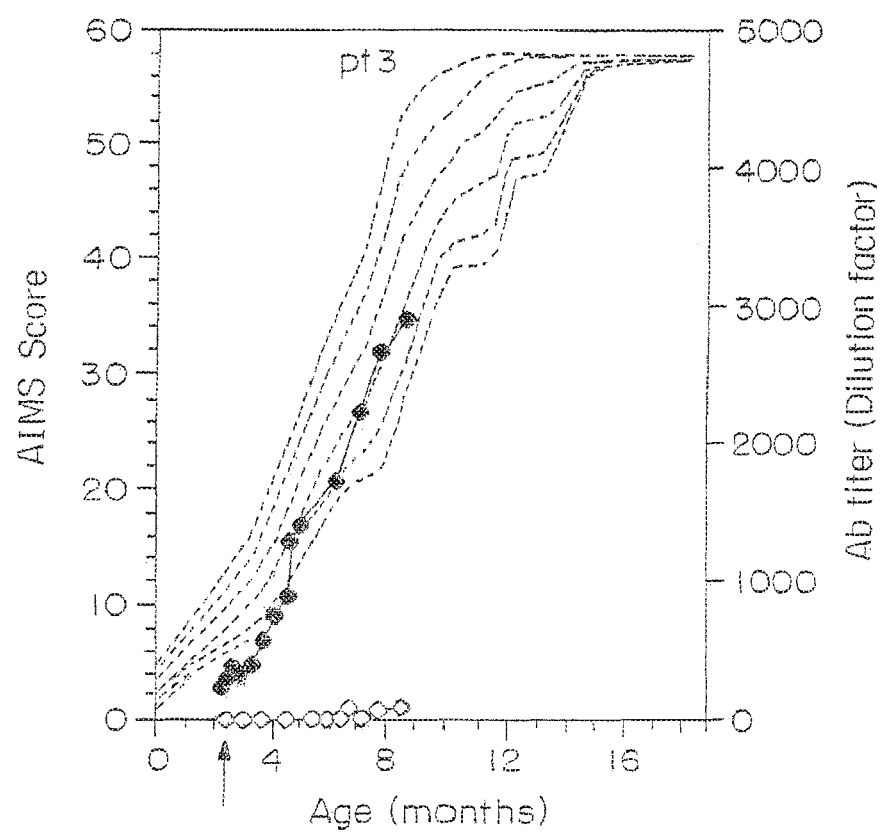

Anti-rhGAA antibodies of IgG class were detected in patients 1 and 2 as early as 3 weeks after the initiation of the enzyme therapy (FIGS. 1A-1C). Anti-rhGAA antibody titers increased to 1:1600 by week 16 in patient 1 (FIG. 1A) and 1:6400-1:12,800 between weeks 11-19 in patient 2 (FIG. 1B). As anti-rhGAA antibody titers increased, we noted that clinical improvements (noted early during therapy—see below) were no longer advancing. Neither untoward effects nor anti-rhGAA antibodies have been detected in patient 3 (FIG. 1C).

Figure 2A:
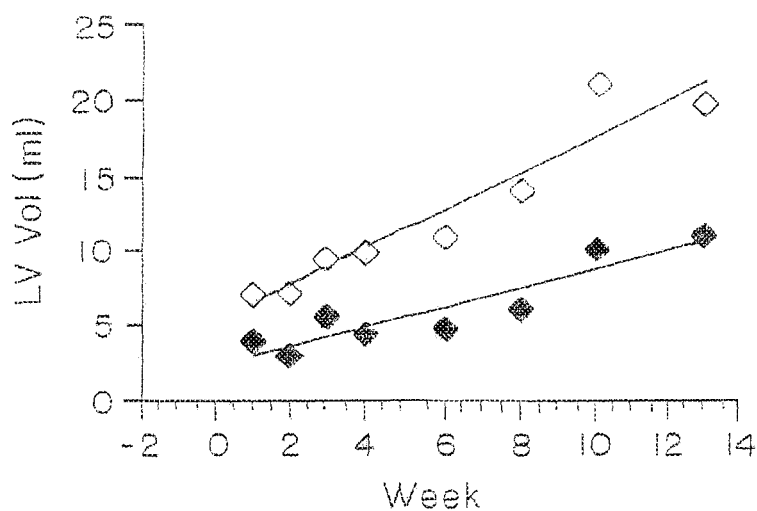
FIG. 2A-2F are a series of graphic representations depicting longitudinal two-dimensional echocardiographic measurements of left ventricular volume (FIGS. 2A-2C) and mass (FIGS. 2D-2F) in the three infantile Pompe disease patients receiving enzyme replacement therapy (patient 1, FIGS. 2A and 2D; patient 2, FIGS. 2B and 2E; patient 3, FIGS. 2C and 2F). Week 0 depicts the measurements at the time of enzyme therapy initiation. Open diamonds, end-diastolic volume measurement; closed diamonds, end-systolic volume measurement.
Figure 2B:
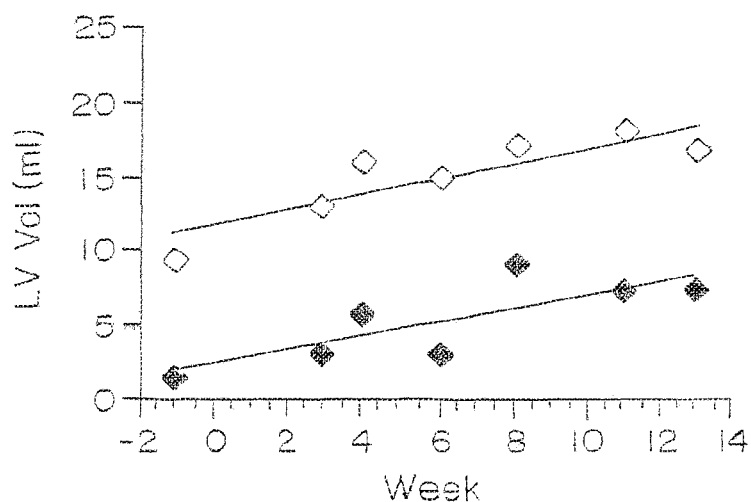
Figure 2C:
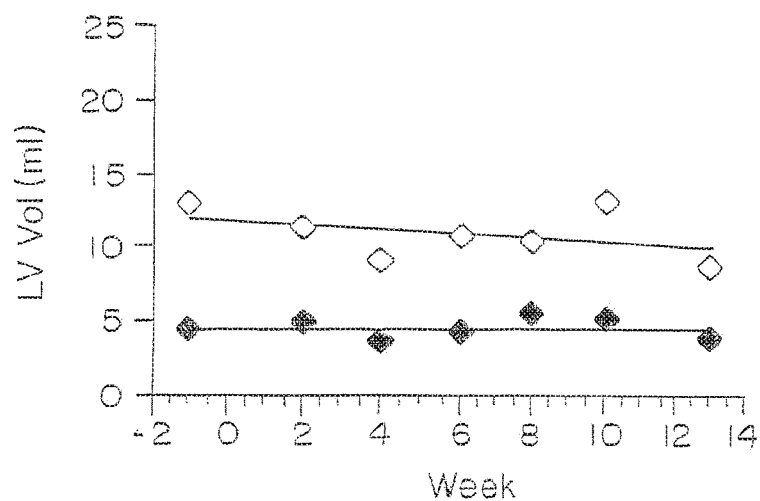
Figure 2D:
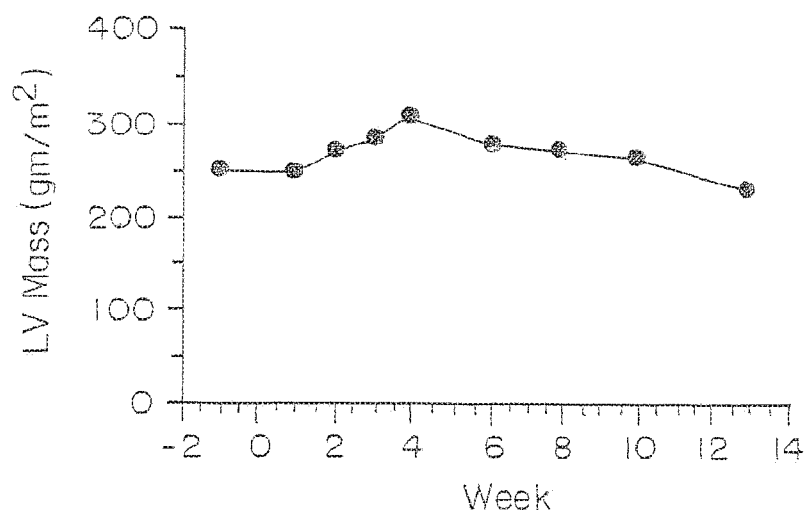
Figure 2E:
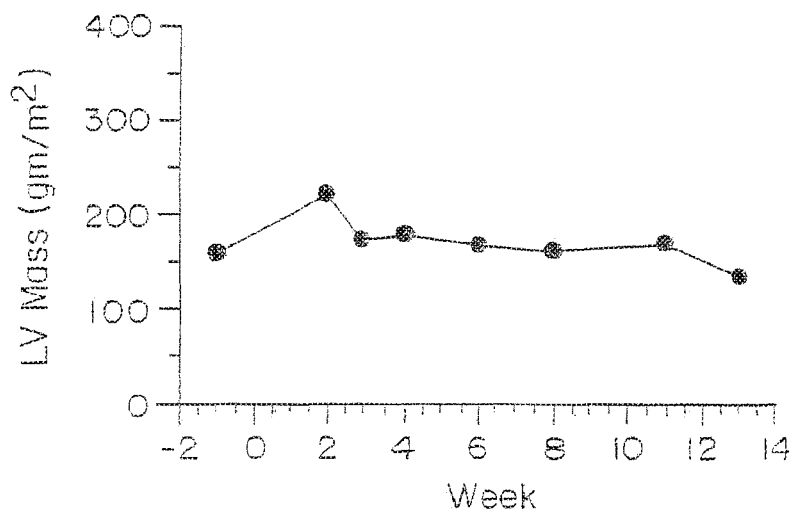
Figure 2F:
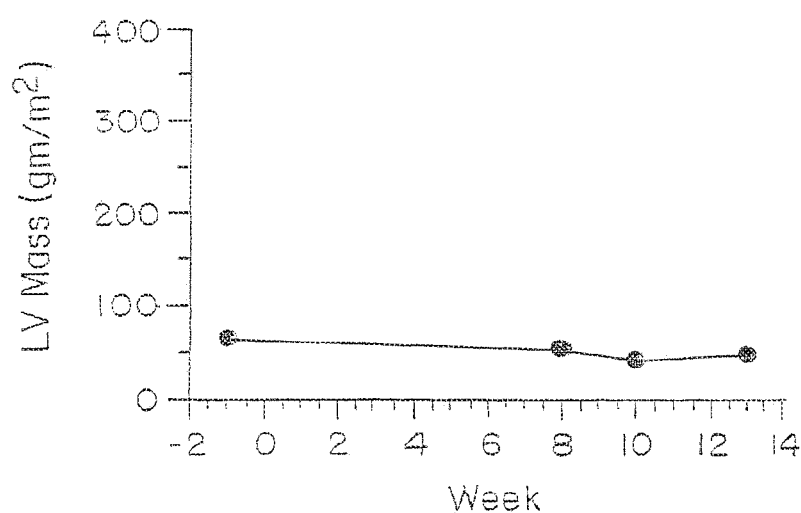

Cardiac status: Prior to the initiation of the enzyme therapy, patients 1 and 2 had severe hypertrophic cardiomyopathy associated with an increased left ventricular (LV) mass, concentric thickening of the ventricular wall and a decrease in size of the ventricular cavity (FIG. 2B, the cavity in patient 2 was almost obliterated at the end of systole). All of these features are typically seen in the untreated patient with the infantile form of Pompe disease. Additionally patient 2 was noted to have an increased LV ejection fraction (shortening fraction, 84%) reflective of a hyperdynamic shortening. None of the patients, however, had any evidence of obstruction of the ventricular outflow tract. The longitudinal echocardiography data assessed in the patients during the first 3 months of rhGAA therapy are shown in FIG. 2A-2C. During the treatment period, in both patients 1 and 2, the LV end-diastolic and end-systolic volumes (2-D measurements) progressively increased, and up to almost 2-3 fold by the end of 3 months of therapy as compared to those measured during the pre-treatment phase (FIGS. 2A and 2B, respectively). Similar increases were noted by M-mode analysis (data not show). The two-dimensional LV mass measurements (FIG. 2D-2F) initially increased as the LV volumes increased, but then steadily decreased during therapy, to a value that was less than the pre-treatment LV mass (reduced to 60-70% of the baseline pretreatment levels). The initial increase in mass was most likely due to an increase in the LV volume, without any changes in the LV wall thickness. These overall improvements in cardiac parameters, were sustained through the latest follow-up evaluation, although patient 1 required an intensive daily enzyme infusion for 10 days when LV mass was further increased and cardiac function compromised at the time of viral pneumonia. Otherwise the ventricular function in both patients had been normal and remained normal at the latest follow-up. Thus, the progressive cardiac morbidity normally noted in untreated infantile Pompe disease was clearly averted.

Patient 3 had a Lv mass of 64 g/$\beta^2$ (upper normal limits 65) but otherwise of normal baseline cardiac evaluation at the initiation of therapy, and has continued to be normal (with LV mass now of 33 g/$\beta^2$) since 7 months post-therapy.

Pulmonary function: In the first 2 months of therapy, improvement of pulmonary function was evident by increases in crying vital capacity (improvements of greater than 28% and 70%, in patients 1 and 2, respectively) over baseline capacities, and normalization of $O_2$ desaturation during crying ($O_2$ saturation of 70% in patient 1 and 81% in patient 2 during maximal crying). Decreased respiratory muscle strength was also evidenced in patient 1 before the therapy by a negative inspiratory force maneuver (NIFM) of −45 cm $H_2O$. With treatment, the NIFM increased to −55 cm $H_2O$. The initial improvements noted in the pulmonary functions of both patients, however, plateaued over the next 2-3 months and declined subsequently, concomitant with the rising anti-rhGAA antibodies. Both patients have subsequently become ventilator dependent after episodes of viral pneumonia precipitated respiratory insufficiency.

Patient 3 had a normal pulmonary function at initiation of therapy and has continued to demonstrate normal pulmonary function testing at the latest follow-up.

Neurodevelopment and motor assessment: Alberta Infant Motor Scale (AIMS) was used to evaluate the motor development in these infants. AIMS scores for all 3 patients started below the 5th percentile for age (FIG. 1A-1C). Patient 1 remained below the 5th percentile but showed increases within that range before beginning to decline at week 13 of the therapy (FIG. 1A). Patient 2 rose to the 25th percentile by week 5, dropped back to remain below the 5th percentile after week 7 despite increasing skills, then showed a rapid decline and loss of skills between weeks 13 and 17 (FIG. 1B). The onset of clinical declines, again was concomitant with the rising anti-rhGAA antibodies (FIG. 1A, 1B).

Concurrently administered neurologic and Denver Developmental evaluations showed in patient 1, normal personal-social, language, and fine motor developmental domains with ongoing but improving gross motor delay until week 10 when a plateau and subsequent regression became apparent. Importantly, gross motor skills had shown significant progress until week 10 but never reached normal. Patient 2 showed mild developmental delay in the gross motor sphere only with attainment of normal developmental skills in the fine motor, personal-social, and language domains until weeks 14-16 when regression occurred. Currently, both patients have normal personal-social development for age but delay in all other domains.

Patient 3 showed a steady increase of AIMS score, rising over the $10^{th}$ percentile by week 11 of the therapy and rising above the $25^{th}$ percentile by week 20 (FIG. 1C), and $90^{th}$ percentile at latest follow-up. At age 9 months, he maintained independent sitting, belly crawled reciprocally for mobility, and maintained standing with hands held. Remarkably, he has been walking independently since 12 months of age and has been able to move between squatting and standing without hand use since 14 months of age. He currently also has normal for age neurologic and Denver development evaluations in all domains.

Muscle GAA activity and glycogen content: Muscle biopsies were performed at baseline 1 week prior to the start of the rhGAA therapy except in patient 1 who had a biopsy done at the time of diagnosis which was 2 months prior to initiation of rhGAA therapy. After 4 months of rhGAA therapy, muscle biopsies were obtained from the contralateral quadriceps 3 days after the enzyme infusion (trough level). With rhGAA treatment GAA activity increased 2-3 fold over baseline pre-treatment levels in both patients 1 and 2, and 18 fold in patient 3 (Table 3).

TABLE 3

Muscle Acid α-glucosidase Activity and Glycogen Content in Infantile Pompe Disease Patients Treated with rhGAA

|  | GAA Activity nmole/hr/mg Protein | Glycogen Content % Wet Weight |
|---|---|---|
| Patient 1 | | |
| Pre-therapy | 0.41 | 5.90% |
| Post-therapy | 0.95 | 7.50% |
| Patient 2 | | |
| Pre-therapy | 0.67 | 5.68% |
| Post-therapy | 1.97 | 4.43% |
| Patient 3 | | |
| Pre-therapy | 0.1 | 5.13% |
| Post-therapy | 1.84 | 1.43% |
| Control | 23.92 +/− 8.63 | 0.94 +/− 0.55% (upper normal limit; 1.5%) |

The absolute level of GAA activity approached 8% of the GAA activity seen in normal muscles. There were no appreciable changes in the muscle glycogen content in patients 1 and 2, but glycogen levels were reduced to within normal range in patient 3.

Histology. The pre-treatment biopsies of all the patients showed marked vacuolization of the muscle fibers in the frozen sections. Evaluation of the semithin sections demonstrated the fibers to be expanded by glycogen with the formation of glycogen lakes. In some fibers faint outlines of residual membranes could be discerned. Electron microscopy confirmed the presence of glycogen both in expanded lysosomes and lying free in the cytoplasm. The biopsy from patient 3 had more glycogen remaining within lysosomes than did the other two patients (data not shown).

The 4-month post-treatment biopsies of patients 1 and 2 were similar to the pre-treatment biopsies in terms of glycogen accumulation. The post-treatment biopsy of patient 3, however, had a marked decrease in visible glycogen and essentially normal histology in most of the muscle fibers. Electron microscopy showed many remaining distended lysosomes were depleted of glycogen. Some glycogen lakes and glycogen-rich lysosomes remained.

Western Blot Analysis

To investigate why anti-rhGAA antibodies developed in patients 1 and 2, but not 3, we performed a Western blot analysis specific for detection of expressed (but nonfunctional) GAA protein in fibroblasts derived from each of the patients. No GAA protein was detected in the fibroblasts of patients 1 and 2, whereas a readily detectable precursor form of GAA protein (110 kD) was found in patient 3. These patterns were previously seen in other patients with infantile GSD-II (Van der Ploeg, A. T. et al., *Am. J. Hum. Genet.* 44:787-793 (1989)). Normal fibroblasts as expected have GAA protein predominantly of 95 kD and 76 kD.

FURTHER STUDIES

Three more patients have been enrolled in an additional study. All three are CRIM positive. After treatment (10 mg/kilogram body weight, weekly intravenous infusions of rhGAA) for 3-6 weeks, improvement of heart function, muscle strength, and motor development have been seen.

The teachings of all publications cited herein are incorporated herein by reference in their entirety.

While this invention has been particularly shown and described with reference to preferred embodiments thereof, it will be understood by those skilled in the art that various changes in form and details may be made therein without departing from the spirit and scope of the invention as defined by the appended claims.

The invention claimed is:

1. A method of treating glycogen storage disease type II in a human individual having glycogen storage disease type II, comprising administering to the individual a therapeutically effective amount of human acid α-glucosidase periodically at an administration interval, wherein the human acid α-glucosidase is a precursor of recombinant human acid α-glucosidase that has been produced in Chinese hamster ovary cell cultures, and wherein the human acid α-glucosidase has a specific enzyme activity in the range of about 1.0-3.5 μmol/min/mg protein.

2. The method of claim 1, wherein the human acid α-glucosidase has a specific enzyme activity in the range of about 2-3.5 μmol/min/mg protein.

* * * * *